(12) United States Patent
Ogden et al.

(10) Patent No.: US 6,841,350 B2
(45) Date of Patent: Jan. 11, 2005

(54) METHODS OF DIAGNOSING PROSTATE CANCER THROUGH THE DETECTION OF THE PRESENCE OR ABSENCE OF PAX 2 MRNA

(75) Inventors: Christopher William Ogden, London (GB); James Adshead, Old Amsterdam (GB); Anna Maria Kessling, Rickmansworth (GB); Bijan Khoubehi, London (GB)

(73) Assignee: The North West London Hospitals NHS Trust of Northwick Park Hospital, Middlesex (GB)

( * ) Notice: Subject to any disclaimer, the term of this patent is extended or adjusted under 35 U.S.C. 154(b) by 50 days.

(21) Appl. No.: 09/933,548

(22) Filed: Aug. 20, 2001

(65) Prior Publication Data

US 2002/0142320 A1 Oct. 3, 2002

Related U.S. Application Data

(63) Continuation of application No. PCT/GB00/00586, filed on Feb. 21, 2000.

(30) Foreign Application Priority Data

Feb. 20, 1999 (GB) ............................................. 9903841

(51) Int. Cl.[7] .......................... C12Q 1/68; C12P 19/34; C07H 21/02; C07H 21/04
(52) U.S. Cl. ......................... 435/6; 435/91.2; 536/23.5; 536/24.31; 536/24.33
(58) Field of Search ......................... 435/6, 91.1, 91.2; 536/23.1, 24.1, 23.5, 24.3, 24.31

(56) References Cited

U.S. PATENT DOCUMENTS

| | | |
|---|---|---|
| 4,376,110 A | 3/1983 | David et al. |
| 4,486,530 A | 12/1984 | David et al. |
| 5,747,250 A | 5/1998 | Gruss et al. |
| 6,071,697 A | 6/2000 | Sosa-Pineida et al. |

FOREIGN PATENT DOCUMENTS

| | | | |
|---|---|---|---|
| DE | WO 94 03196 | * 2/1994 | ......... A61K/37/02 |
| EP | 0 655 926 B1 | 6/1995 | |
| WO | WO 94/03196 A1 | 2/1994 | |
| WO | WO 95/32214 A1 | 11/1995 | |
| WO | WO 96/02674 A1 | 2/1996 | |
| WO | WO 97/15686 A1 | 5/1997 | |

OTHER PUBLICATIONS

Gray et al. Cancer Research 55, 4800–4803, Nov. 1, 1995.*
Adams, et at., "Pax–5 encodes the transcription factor BSAP and is expressed in B lymphocytes, the developing CNS, and adult testes," *Genes & Development* 6:1589–1607 (1992).
Balaguer, et at., "Quantification of DNA sequences obtained by polymerase chain reaction using a bioluminescent adsorbent," *Analytical Biochemistry* 195:105–110 (1991).
Bernasconi, et al., "Induction of apoptosis in rhabdomyosarcoma cells through down–regualtion of PAX proteins," *Proc Natl Acad Sci USA* 93:13164–69 (1996).

(List continued on next page.)

*Primary Examiner*—Carla J. Myers
*Assistant Examiner*—Sally A Sakelaris
(74) *Attorney, Agent, or Firm*—Pabst Patent Group LLP

(57) ABSTRACT

A method of diagnosing prostate cancer in a human patient comprising the steps of obtaining a sample containing nucleic acid and/or protein from prostate cells of a patient, and determining whether the sample contains a level of Pax 2 nucleic acid or protein associated with prostate cancer. A method of treating prostate cancer comprising the step of administering to the patient an agent which selectively prevents the function of Pax 2. A genetic construct comprising a nucleic acid encoding a molecule capable of preventing the function of Pax 2 expressed in a prostate cell.

16 Claims, 14 Drawing Sheets

OTHER PUBLICATIONS

Figure 1A:
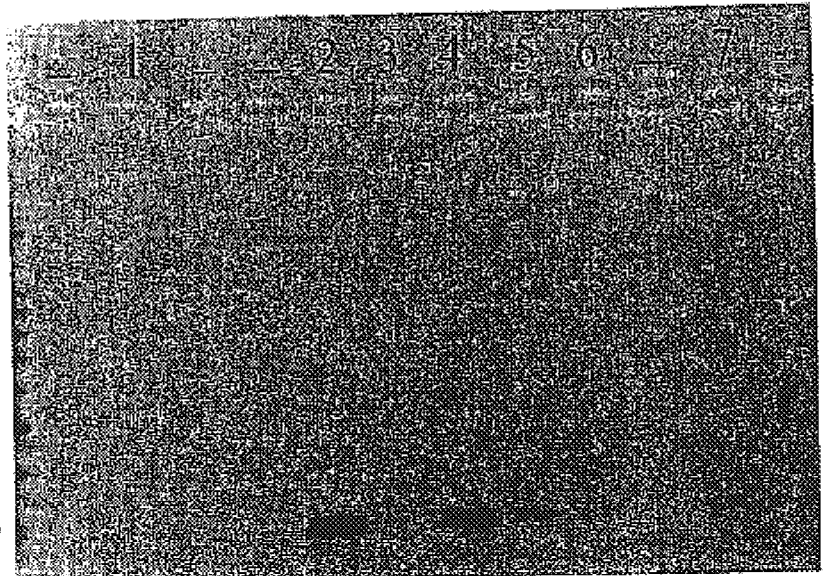

Bischoff, et al., "An adventure mutant that replicates selectively in p53–deficient human tumor cells," *Science* 274:373–376 (1996).

Brawer, "Prostate Specific Antigen," *Acta Oncol.* 30:161–168 (1991).

Brothman, et al., "Frequency and pattern of karyotypic abnormalities in human prostate cancer," *Cancer Research* 50:3795–3803 (1990).

Busslinger, at al., "The role of BSAP (Pax–5) in B–cell development." *Current Opinion in Genetics and Development* 5:595–601 (1995).

*Cancer Statistics: Registrations* Engalnd and Wales OPCS MWI No. 22, Her Majesty's Stationery Office (1994).

Cannon–Albright & Eeles, "Progress in prostate cancer," *Nature Genetics* 9:336–338 (1995).

Chamberlain, et al., "Report prepared for the health technology assessment panel of the NHS execution on the diagnosis, management, treatment and costs of prostate cancer an England and Wales," *British Journal of Urology* 79(Suppl.3):1–32 (1997).

Chan, et al., "Plasma insulin–like growth factor–1 and prostate cancer risk: a prospective study," *Science* 279:563–566 (1998).

Compton, Nucleic acid sequence–based amplification, *Nature* 350:91–92 (1991).

Cotten, et al., "High–efficiency receptor–mediated delivery of small and large (48 kilobase) gene constructs using the endosome–disruption activity of detective or chemically inactivated adenovirus particles," *Proc Natl Acad Sci USA* 89:6094–6098 (1992).

Culver, et al.. "In vivo gene transfer with retroviral vector-producer cells for treatment of experimental brain tumors," *Science* 256:1550–1552 (1992).

Curiel, "Adenovirus facilitation of molecular conjugate–mediated gene transfer," Prog Med Virol 40:1–18 (1993).

Dicesare, et al., "A high–sensitivity electrochemiluminescence–based detection system for automated PCR product quantitation," *BioTechniques* 15:152–157 (1993).

Dressler, et al., "Deregulation of *Pax*–2 expression in transgenic mice generates severe kidney abnormalities," *Nature* 362:665–67 (1993).

Dressler, et at., "Pax2, a new murine paired–box–containing gene and its expression in the developing excretory system," *Development* 109(4): 787–795 (1990).

*Future Oncology* "Prostate Cancer–Part II: Diagnosis, Staging, Prognosis, Screening, and Novel Molecular Markers," 3(12): 1998.

Gann, et al., "A prospective evaluation of plasma prostate–specific antigen for detection of prostatic cancer," *JAMA* 273: 289–294 (1995).

Gao, et al., "Diagnostic and prognostic markers for human prostate cancer," *The Prostate* 31:264–281 (1997).

Gao, et al., "High frequency of mutator phenotype in human prostatic adenocarcinoma," *Oncogene* 9:2999–3003 (1994).

Gleason, "Classification of prostatic carcinomas," *Cancer Chemother Rep.* 50:125–128 (1966).

Gnarra & Dressler, "Expression of Pax–2 in human renal cell carninoma and growth inhibition by antisense oligonucleotides," *Cancer Research* 55(18):4092–8 (1995).

Jacobs, at al., "Tharmal stability of oligonucleotide duplexes is sequence independent in tetraalkylammonium application to identifying recombinant DNA clones," *Nucl. Acids Res.* 16:4367 (1988).

Khoubehi, et al., "The expression of the PAX2 in human prostate cancer," *Am J Human Genetics* 65(Suppl. 4):A132 (1999).

Khoubehi, et al., "Expression of the developmental and oncogenic PAX2 gene in human prostate cancer," *J Urology* 165(6.1): 2115–2120.

Koontz, et al., "Mitomycin, for patients who have failed on thiotepa," *Urology* 26(4 Suppl.):30–31 (1985).

Kuriyama, et al., "A Potential approach for gene therapy targeting hepatoma using a liver–specific promoter on a retroviral vector," *Cell Structure and Function* 16:503–510 (1991).

Ledley, "Nonviral gene therapy: The promise of genes as pharmaceutical products," *Human Gene Therapy* 6:1129–1144 (1995).

Li, et al., "PTEN, a putative Protein tyrosine phosphatase gene mutated in human brain, breast, and prostate cancer," *Science* 275:1943–1947 (1997).

Lundwall, "Characterization of the gene for prostate–specific antigen, a human glandular kallikrein," *Biochem. Biophys. Res. Comm.* 161(3): 1151–1159 (1989).

Martin & Papahadjopoulos, et al., "Irreversible coupling of immunoglobulin fragments to preformed vesicles," *J Biol Chem* 257:286–88 (1982).

Massenkeil, et al., "P53 mutations and loss of heterozygosity on chromosomes 8p, 16q, I7p, and 18q are confined to advanced prostate cancer," *Anticancer Res.* 14(6B): 2785–2790 (1994).

Maulbecker & Gruss, "The oncogenic potential of Pax genes," *EMBO JournaI* 12(6): 2361–2367 (1993).

Michael, et al., "Addition of a short peptide ligand to the adenovirus fiber protein," *Gene Therapy* 2:660–668 (1982).

Miller & Vile, "Targeted vectors for gene therapy," *FASEB Journal* 9(2): 190–199 (1995).

*Mortality Statistics: Cause.* England and Wales. OPCS DH2 19, Her Majesty's Stationary Office, 1993.

Nassander, et at., "In vivo targeting of OV–TL 3 immunoliposomes to Ascitic ovarian carcinoma cells (OVCAR–3) in athymic nude mice," *Cancer Research* 52:646–653 (1992).

Nihel, et al., "Localization of metastasis suppressor gene(s) for rat prostatic cancer to the long arm of human chromosome 10," *Genes, Chromosomes & Cancer* 14(2): 112–119 (1995).

Phelps & Dressler, "Aberrant expression of Pax–2 in Danforth's short tail (Sd) mice," *Developmental Biology* 157(1): 251–258 (1993).

Pogrebniak, et al., "Targetted phototherapy with sensitizer-monoclonal antibody conjugate and light," *Surgical Oncology* 2(1): 31–42, 1993.

Riegman, et al., "Characterization of the prostate–specific antigen gene: a novel human kallikrein–like gene," *Biochem Biophys. Res. Comm.* 159(1): 95–102 (1989).

Ryan, et al., "Repression at Pax–2 by WT1 during normal kidney development," *Development* 121: 867–875 (1995).

Saiki, et al., "Primer–directed enzymatic amplification of DNA with a thermostable DNA polymerase," *Science* 239:487–491 (1988).

Sanyanusin, et al., "Fenomic structure of the human PAX2 gene," *Genomics* 35(1): 258–261 (1996).

Schäfer, et al., "Molecular cloning and characterization of a human PAX–7 cDNA expressed in normal and neoplastic myocytes," *Nuc. Acids Res.* 22(22): 4574–4582 (1994).

Smith & Catalona, "Interexaminer variability of digital rectal examination in detecting prostate cancer," *Urology* 45(1): 70–74 (1995).

Steck, et al., "Indentification of a candidate tumour suppressor gene, MMAC1, at chromosome 10q23.3 that is mutated in multiple advanced cancers," *Nature Genetics* 15: 356–363 (1997).

Stuart & Gruss, "PAX genes: What's new in developmental biology and cancer?" *Human Mol. Gen.* 4: 1717–1720 (1995).

Stuart, et al, "Loss of p53 funtion through PAX–mediated transcriptional repression," *EMBO Journal* 14: 5638–5645 (1995).

Stuart, et al., "Mammalian PAX genes," *Annu Rev. Genet.* 27: 219–236 (1993).

Stuart, et al., "PAX and HOX in Neoplasia," *Adv. Genet.* 33: 255–274 (1995).

Wagner, et al., "Transferrin—polycation conjugates as carriers for DNA uptake into cells," *Proc. Nat. Acad. Sci. USA* 87: 3410–3414 (1990).

Walker, et al., "Strand displacement amplification—an isothermal, in vitro DNA amplification technique," *Nuc. Acids. Res.* 20(7): 1691–1696 (1992).

Yarmush, et al., "Antibody targeted photolysis," *Crit. Rev. Therap. Drug Carrier Syst.* 10(3): 197–252 (1993).

Zenklusen, et al., "Loss of heterozygosity in human primary prostate carcinomas: A possible tumor suppressor gene at 7q31.1." *Cancer Res.* 54: 6370–6373 (1994).

* cited by examiner

300 Base pair →

The PAX2 expression in 3 out of 5 channel TURP specimens.

Lane 1    negative control (water)
Lane 2-6  channel TURPs (i.e prostate cancers)
Lane 7    positive control (OUK 117)

—    blank lanes

Lack of expression of PAX 2 in 10 Benign Prostatic \Hypertrophy specimens 300 base pair Lanes 1-10: the 10 benign prostatic hypertrophy specimens
lane 12: Positive control (UOK 117)
Lane 14: negative control (water)
Lanes - Blank

GAPDH RTPCR of the 10 Benign Prostatic Hypertrophy speciemens

← 200 Base pair

Lanes 1-10: Ten Benign samples
Lane 12: Negative control (water)
Lanes -: Blank lanes

GAPDH RTPCR of the Cell Lines

Lane 1: LNCaP
Lane 2: DU145
Lane 3: PC3
Lanes -: Blank
Lane 5: Negative Control (water)

Expression of PAX2 in tumours 1,3,7,14,16,19,21,25,26.

300 base pair

The Lanes are marked with the number given to each tumour.
UOK117 is the positive control. Water is the negative control.

Southern hybridisation
of the above gel

GAPDH expression in tumours 24, 27, 32, 38, 41 and 43

200 Base pair

The Lanes are marked with the number given to each tumour.
Water is the negative control.

Figure 3A:
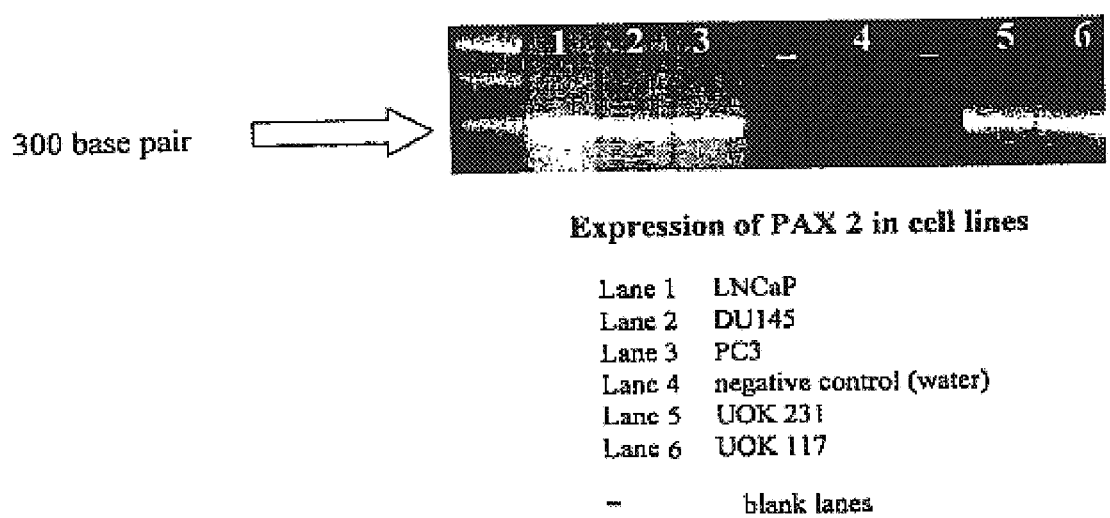
Figure 3B:
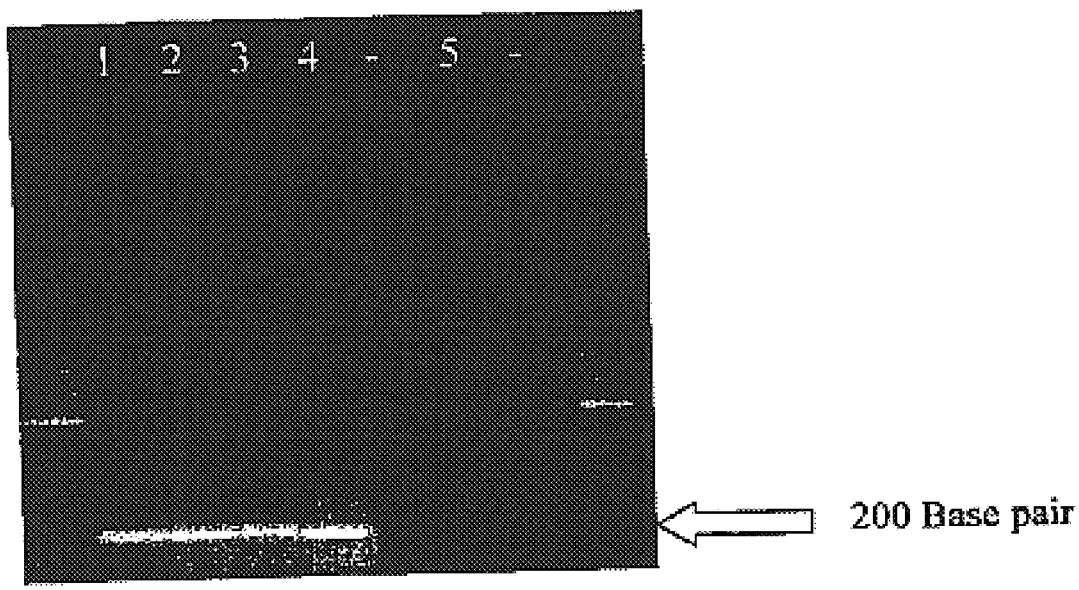
Figure 4A:
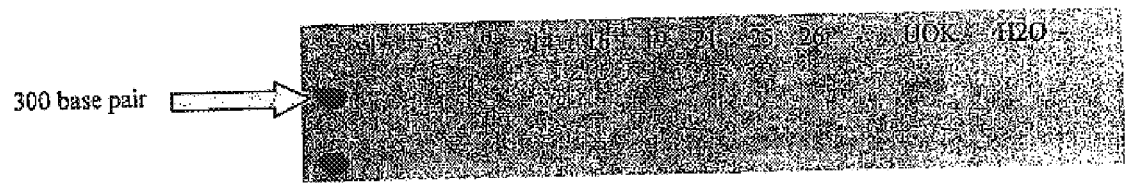
Figure 4A:
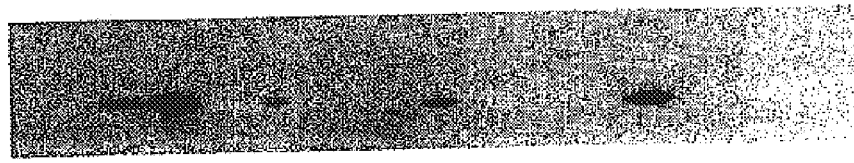
Figure 4B:
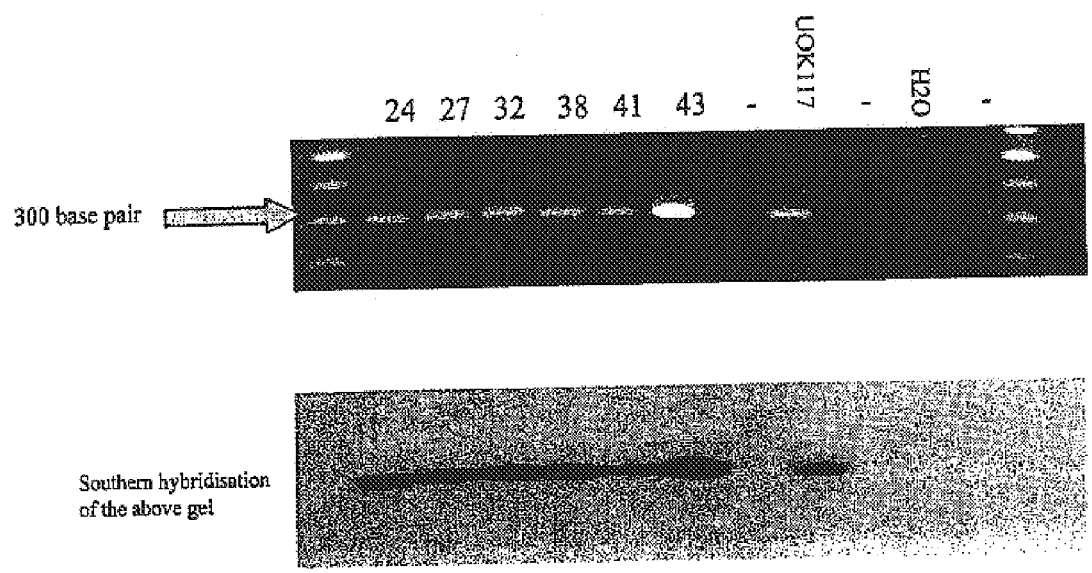
Figure 4C:
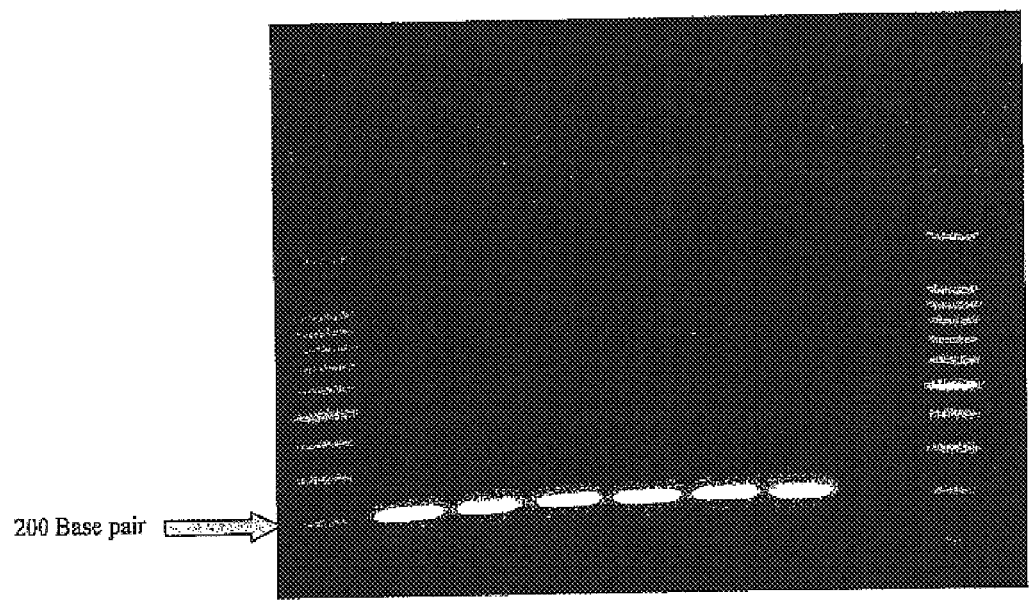
Figure 5A:
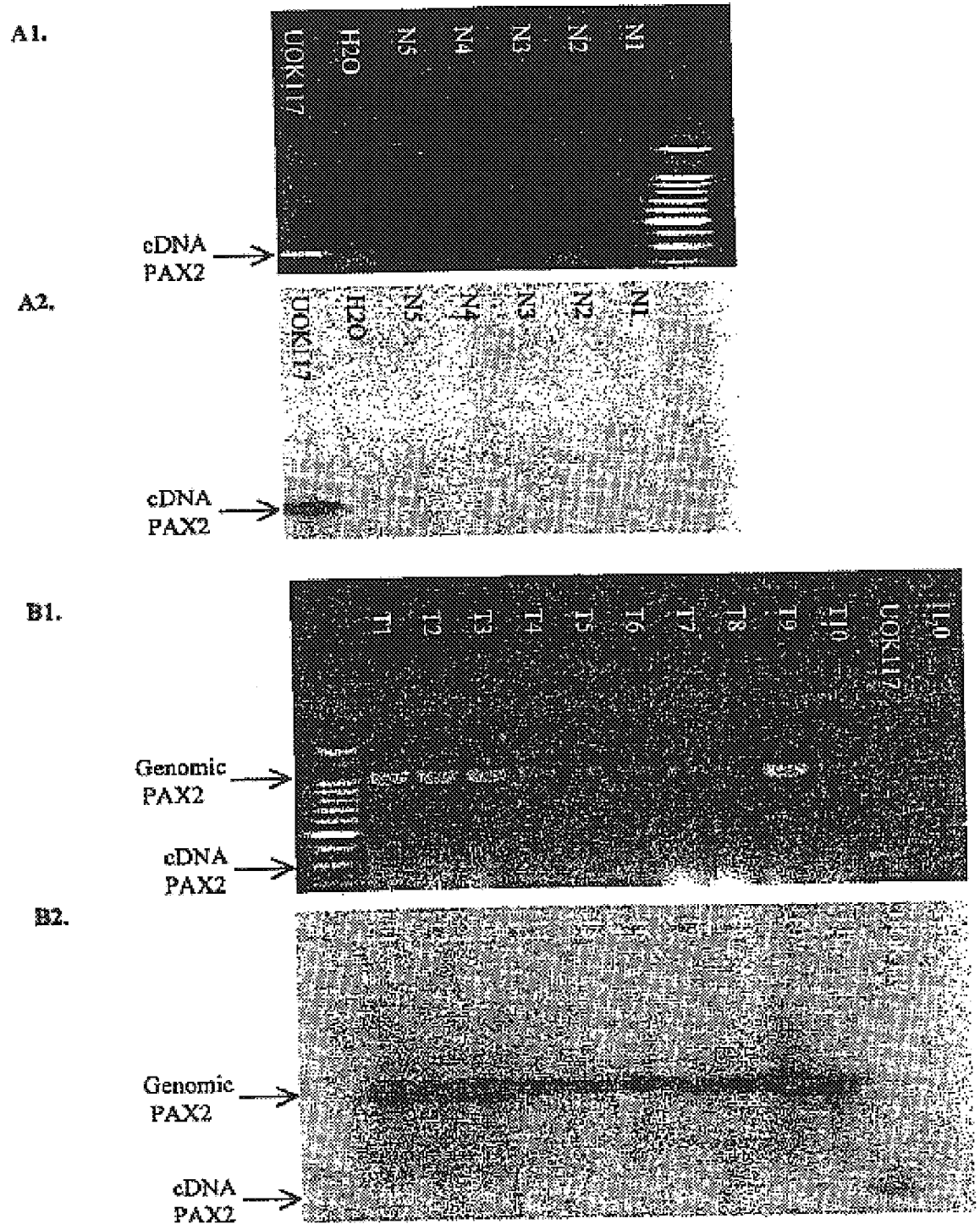

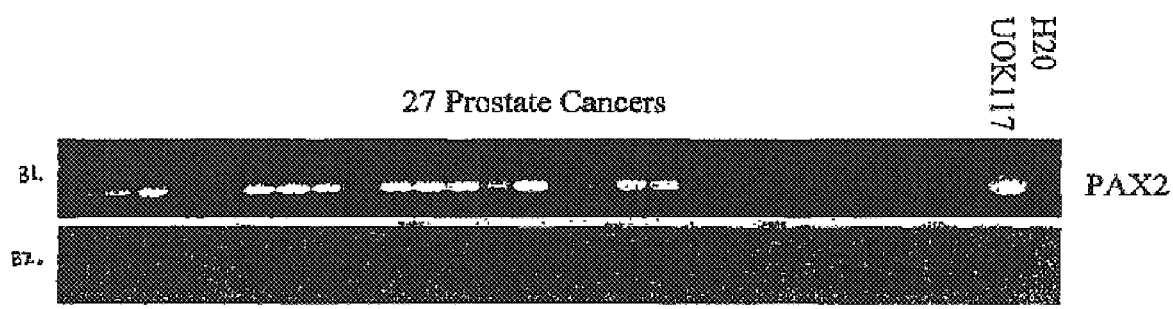
Fig. 5A3

METHODS OF DIAGNOSING PROSTATE CANCER THROUGH THE DETECTION OF THE PRESENCE OR ABSENCE OF PAX 2 MRNA

This application is a continuation of PCT/GB00/00586 filed Feb. 21, 2000.

The present invention relates to methods of determining whether a patient has cancer and how advanced or invasive that cancer is; and it relates to methods of treating prostate cancer.

Cancer is a serious disease and a major killer. Although there have been advances in the diagnosis and treatment of certain cancers in recent years, there is still a need for improvements in diagnosis and treatment.

Cancer is a genetic disease and in most cases involves mutations in one or more genes. There are believed to be around 200,000 genes in the human genome but only a handful of these genes have been shown to be involved in cancer. Although it is surmised that many more genes than have been presently identified will be found to be involved in cancer, progress in this area has remained slow despite the availability of molecular analytical techniques. This may be due to the varied structure and function of genes which have been identified to date which suggests that cancer genes can take many forms and have many different functions.

Carcinoma of the prostate has become a most significant disease in many countries and it is the most commonly diagnosed malignancy in men in the western world, its occurrence increasing significantly with age. Over the last 20 years the mortality rates have doubled and it is now the second commonest cause of male cancer deaths in England and Wales (Mortality Statistics: Cause. England and Wales. OPCS DH2 19, 1993, Her Majesty's Stationery Office). The prevalence of prostate cancer has increased by 28% in the last decade and this disease now accounts for 12% of the total cancers of men in England and Wales (Cancer Statistics: Registrations England and Wales. OPCS MBI No 22, 1994, Her Majesty's Stationery Office). By the year 2018 it is expected to be the biggest killer, affecting 50% of the male population (80% by age 80 years). This increase and the recent deaths of many public figures from prostate cancer have served to highlight the need to do something about this cancer. It has been suggested that the wider availability of screening may limit mortality from prostate cancer.

Prostate cancer screening currently consists of a rectal examination and measurement of prostate specific antigen (PSA) levels. These methods lack specificity as digital rectal examination has considerable inter-examiner variability (Smith & Catalona (1995) *Urology* 45, 70–74) and PSA levels may be elevated in benign prostatic hyperplasia (BPH), prostatic inflammation and other conditions. The comparative failure of PSA as a diagnostic test was shown in 366 men who developed prostate cancer while being included in the Physicians Health Study, a prospective study of over 22,000 men. PSA levels were measured in serum, which was stored at the start of the study, and elevated levels were found in only 47% of men developing prostate cancer within the subsequent four years (Gann et al (1995) *JAMA* 273, 289–294).

Lung metastasis may be assessed by chest X-rays. Bone metastases may be detected, for example, by radiological imaging.

Prostate cancer diagnosis is reviewed in *Future Oncol* (1998) 3(12), 762–769 "Prostate cancer—Part II—Diagnosis, staging, prognosis, screening, and novel molecular markers". Markers that may be used in diagnosis and prognosis of prostate cancer are reviewed in Gao et al (1997) *The Prostate* 31, 264–281. Diagnosis, biopsy and surgical techniques are described in "Surgery of the prostate" Ed Resnick & Thompson (1998) Churchill Livingstone, incorporated herein by reference.

Prostate cancers may be scored using the Gleason system, as well known to those skilled in the art (Gleason (1966) "Classification of prostatic carcinomas" *Cancer Chemother Rep* 50, 125–128). This uses tissue architecture rather than cytological features. A grade of 1 to 5 (well to poorly differentiated) is used, and the combined score of the most frequent and more severe areas of the lesion are combined. Gleason scores provide prognostic information that may be valuable in addition to the assessment of the stage of the tumour (staging). Gleason scores of 2 to 4 and 8 to 10 have good predictive value, but about three quarters of tumours have intermediate values.

Two principal systems are used for staging prostate cancer: TNM and the Jewett system (Benson & Olsson (1989) "The staging and grading of prostatic cancer" in *The Prostate*, ed Fitzpatrick, J. M. and Krane R. J. pp 261–272, Edinburgh, Churchill Livingstone). Staging takes in to account any metastatic spread of the tumour and is difficult, because it is difficult to assess either local lymph node involvement or local invasion. Tumour size is also difficult to measure as tumour tissue cannot be distinguished macroscopically from normal prostate tissue, and because the prostate gland lacks a distinct capsule and is surrounded by a layer of fibrous fatty tissue. Tumours may be classified as T1 to T4.

Present screening methods may therefore be unsatisfactory; there is no reliable method for diagnosing the cancer, or predicting or preventing its possible metastatic spread, which is the main cause of death for most patients.

Pax genes are a family of nine developmental control genes coding for nuclear transcription factors. They play an important role in embryogenesis and are expressed in a very ordered temporal and spatial pattern. They all contain a "paired box" region of 384 base pairs encoding a DNA binding domain which is highly conserved throughout evolution (Stuart E T et al Mammalian Pax genes. Annual Review of Genetics 1994;28(219):219–36). The influence of Pax genes on developmental processes has been demonstrated by the numerous natural mouse and human syndromes that can be attributed directly to even a heterozygous insufficiency in a Pax gene (Stuart E T et al (1994)). Their role in controlling cell growth and proliferation in such a regulated fashion has lead to the investigation of their involvement in the deregulated growth seen in neoplasia.

The subgroup of Pax 2, 5, and 8 (class III) are expressed latest in development and only in the undifferentiated, highly mitotic cells of the ventricular zone of the CNS (Pax 2, 5 and 8), the developing kidney (Stuart E T, Gruss P. PAX genes: what's new in developmental biology and cancer?. Human Molecular Genetics 1995; 1717 and Stuart E T et al. (1994)), B-cell progenitors (Koontz W I, Heney N M, Soloway M S, et al. Mitomycin for patients who have failed on thiotepa. The National Bladder Cancer Group. Urology 1985; October 26(4 Suppl):30–31.) and the thyroid (Stuart E T et al. (1994)). In mice, after birth, Pax 5 is expressed exclusively in B cells and testis (Busslinger M, Urbanek P. The role of BSAP (Pax-5) in B-cell development. Current Opinion in Genetics & Development 1995;5(5):595–601).

Because of the powerful effect of these transcription factors on cellular growth and differentiation and the salient feature of expression for Pax 2, 5 and 8 in highly mitotic, undifferentiated cells they are candidates for proto-oncogenes. Pax genes are capable of transforming fibroblasts and producing solid, vascular tumours in nude mice (Maulbecker C C, Gruss P. The oncogenetic potential of Pax genes. Embo J 1993;12(6):2361–7). They have been shown to be inappropriately expressed in many different tumours eg glioblastoma (Pax 5), renal cell carcinoma (Pax 2), medulloblastoma, non-Hodgkins lymphoma (Pax 5), Wilm's tumour (Pax 2 and 8) and rhabdomyosarcoma (Pax 3 and 7) (reviewed in Stuart E T et al. PAX and HOX in neoplasia. Advances in Genetics 1995;33(255):255–74). EP 0 655 926 relates to the involvement of Pax genes in cancer.

In vitro studies have shown that antisense to Pax 2 in renal cell lines expressing this gene considerably hinders growth. Pax 2 has an important role in the pathogenesis of Wilm's tumour and renal cell carcinoma and is transcriptionally repressed by the Wilm's tumour suppressor gene. Pax 2 has a crucial role in the development of the urogenital system to the extent that Pax 2 homozygous mutant newborn mice lack kidneys, ureters and genital tracts. Pax 2 is expressed at high levels in human Wilm's tumour and is a proto-oncogene in mice, which suggests a link between its role as a developmental gene and tumorigenesis. The human Pax 2 gene is located on chromosome 10 at 10q25.

Despite considerable research, a genetic marker that is useful in reliably predicting the outcome of prostate cancer has not been identified. It is now shown that Pax 2 expression has a role in the pathogenesis of prostate cancer. The expression of Pax 2 in prostate cancer cell lines and in prostate cancer specimens but not in benign prostate hyperplasia specimens may indicate a role for Pax 2 in supporting cellular proliferation in the de-differentiated state in prostate cancer. Pax 2 may therefore be an important diagnostic marker of prostate cancer and indicator of likely progression as well as a therapeutic target.

As noted above, Pax 2 is a known protein (although not previously known to be associated with prostate cancer) and the amino acid sequence of the protein, and nucleotide sequence of the gene and mRNA encoding it are known (Sanyanusin P et al (1996) Genomic structure of the PAX2 gene *Genomics* 35(1), 258–261). A Pax 2 sequence is given in Dressler et al (1990) *Development* 109, 787–795.

It is an object of the invention to provide methods useful in providing diagnoses and prognoses of prostate cancer, and for aiding the clinician in the management of prostate cancer. In particular, an object of the invention is to provide a method of assessing the metastatic potential of prostate cancer.

Further objects of the invention include the provision of methods of treatment of prostate cancer, for example using inhibitors of Pax 2 expression or activity, for example using anti-sense based therapy.

A first aspect of the invention provides a method of determining the susceptibility of a patient to prostate cancer comprising the steps of (i) obtaining a sample containing nucleic acid and/or protein from prostate cells of a patient; and (ii) determining whether the sample contains a level of Pax 2 nucleic acid or protein associated with prostate cancer.

A second aspect of the invention provides a method of diagnosing cancer in a human patient comprising the steps of (i) obtaining a sample containing nucleic acid and/or protein from prostate cells of a patient; and (ii) determining whether the sample contains a level of Pax 2 nucleic acid or protein associated with prostate cancer.

It will be appreciated that determining whether the sample contains a level of Pax 2 nucleic acid or protein associated with prostate cancer may in itself be diagnostic of prostate cancer or it may be used by the clinician as an aid in reaching a diagnosis.

For example, in relation to prostate cancer, it is useful if the clinician undertakes a histopathological examination of biopsy tissue or measures plasma PSA level or carries out external digital examination or carries out imaging. Recently, the possibility of using the blood IGF-1 level has also been suggested (Chan et al (1998) *Science* 279, 563–566).

Symptoms that may arise from prostate cancer include urinary obstruction, pelvic pain due to local invasion and metastatic symptoms, including anaemia and bone pain. Urinary obstruction results from pressure on the urethra, but most prostate cancers arise distal from the urethra and do not produce urinary symptoms. Approximately 30% of patients may be diagnosed with symptomatic disease.

It will be appreciated that the clinician will wish to take in to account these or other factors, as well as consider the level of said Pax 2, before making a diagnosis.

Thus, the method may be useful in prognosis or aiding prognosis. The method may be used as an adjunct to known prognostic methods such as histopathological examination of biopsy tissue, or measurement of plasma PSA levels, external digital examination or imaging. Measurement of the rate of change of PSA levels (PSA velocity; PSAV) may be useful. Diagnostic tests and markers that may be useful are described in a review article in *Future Oncology* (1998) 3(12), 762–769, and in Gao et al (1997) *The Prostate* 31, 264–281.

A third aspect of the invention provides a method of predicting the relative prospects of a particular outcome of a prostate cancer in a human patient comprising the steps of (i) obtaining a sample containing nucleic acid and/or protein from prostate cells of the patient; and (ii) determining whether the sample contains a level of Pax 2 nucleic acid or protein associated with cancer. Thus, the method may be useful in prognosis or aiding prognosis. The method may be used as an adjunct to known prognostic methods such as histopathological examination of biopsy tissue, or measurement of plasma PSA levels, external digital examination or imaging.

It will be appreciated that determination of the level of the said Pax 2 in the sample will be useful to the clinician in determining how to manage the cancer in the patient. For example, since elevated levels of the said Pax 2 may be associated with metastatic potential, the clinician may use the information concerning the levels of the said Pax 2 to facilitate decision making regarding treatment of the patient. Thus, if the level of said Pax 2 is indicative of a low metastatic potential of said prostate cancer, unnecessary radical surgery may be avoided. Similarly, if the level of said Pax 2 is indicative of a high metastatic potential of said prostate cancer, radical surgery (ie prostatectomy) may be the preferred treatment.

Curative treatment options may include radical prostatectomy and radiation therapy. Disease management and symptomatic relief options include hormone ablation therapy (HAT, in various forms), radiotherapy, TURP, brachytherapy, chemotherapy and observation without intervention. Patients with metastatic disease treated with HAT usually progress to hormone insensitive disease within 3 years. Treatment of earlier disease with HAT may delay both metastasis and loss of sensitivity. Hormone insensitive metastatic disease may be treated by targeted radiotherapy and analgesics.

Radical prostatectomy is only effective when the disease has not spread outside the prostate or micrometastasised. Difficulty in determining staging of tumours may contribute to difficulties in deciding whether this treatment is appropriate. Not all patients may benefit from treating confined disease given the generally advanced age of patients with prostate cancer. Thus, on average, patients with grade 2 to 4 tumours may have a 95% 10 year metastasis free survival rate following radical prostatectomy, compared with a 75% 10 year metastasis free survival rate following a watchful waiting strategy. For those with grade 8 to 10 tumours, the equivalent figures are 68% and 20%, respectively. It will be appreciated that the relative merits of treatments for prostate cancer are under continual review.

It will be appreciated from the foregoing, and from the Examples below, that the determination of the levels of the said Pax 2 may be exploited diagnostically to predict whether a given cancer of the prostate would metastasise since expression of said Pax 2 is believed to correspond to possible future spread of a tumour.

It is particularly preferred if the method of the invention is employed to predict whether a given cancer of the prostate would metastasise.

The level of said Pax 2 which is indicative of cancer or metastatic potential may be defined as the increased level present in known cancerous or metastatic prostate cells over known non-cancerous or non-metastatic prostate cells. The level may be, for example, at least 1½ fold higher in cancerous cells or metastatic cells, or it may be at least 2-fold or 3-fold higher.

In one preferred embodiment of the invention it is determined whether the level of said Pax 2 nucleic acid, in particular mRNA, is a level associated with cancer. Preferably, the sample contains nucleic acid, such as mRNA, and the level of said Pax 2 is measured by contacting said nucleic acid with a nucleic acid which hybridises selectively to said Pax 2 nucleic acid.

It will be appreciated that Pax 2 may be a pre-malignant marker, such that a change in the expression of Pax 2 may precede other signs of malignancy. Thus if an elevated level of Pax 2 is found in a sample from a patient that has no visible or easily detected signs of prostate cancer, this may indicate that the patient is in the early stages of developing prostate cancer or that the patient may later develop prostate cancer or be particularly susceptible to risk factors for developing prostate cancer, as listed above, for example smoking.

It is preferred that the patient is a human patient. It is preferred if the sample is selected from the group consisting of prostate tissue, blood, urine or semen. Prostate tissue can be obtained from a patient using standard surgical techniques. Samples of prostate may be obtained by surgical excision, laproscopy and biopsy, endoscopy and biopsy, and image-guided biopsy. The image may be generated by ultrasound or technetium-99-labelled antibodies or antibody fragments which bind or locate selectively at the prostate.

Trans-rectal ultrasound(TRUS) can be used to detect cancers that are hypodense (70%) and may be used to guide needle biopsy sections. In the absence of a visible lesion, 4–6 needle biopsies may be taken, divided between the two lobes of the gland. A 1.5 cm biopsy with an 18 gauge needle may sample around 0.03% of the volume of a normal gland.

Transurethral resection (TURP), in which chips of prostate tissue are removed, may be used to relieve benign prostatic hyperplasia and may provide material on which the methods of the present invention may be used. TURP preferentially samples the central and transitional zones of the gland, though cancers of the peripheral zone may also invade the sampled area. 5 to 20% of patients (mainly asymptomatic for prostate cancer) may be found to have prostate cancer by histological analysis of the samples. Patients treated by TURP are generally over 65.

Biopsy methods are described, for example, in Chamberlain et al (1997) *Brit J Urol* 79, suppl 3, 1–32 and WO95/32214.

It is preferred that the sample is obtained using non-invasive procedures. Cells derived from the prostate are found in small numbers in the urine and in the blood. Although it is preferred that the sample containing nucleic acid from the patient is, or is derived directly from, a cell of the patient, such as a prostate cell, a sample indirectly derived from a patient, such as a cell grown in culture, is also included within the invention. Equally, although the nucleic acid derived from the patient may have been physically within the patient, it may alternatively have been copied from nucleic acid which was physically within the patient. The tumour tissue may be taken from the primary tumour or from metastases, and particularly may be taken from the margins of the tumour.

It will be appreciated that the aforementioned methods may be used for presymptomatic screening of a patient who is in a risk group for cancer, particularly prostate cancer. For example, men older than about 60 years are at greater risk of prostate cancer than men below the age of 35. Similarly, the methods may be used for the pathological classification of prostate tumours.

It is preferred that if blood, semen, lymphatic circulation or urine is the source of the said sample containing nucleic acid derived from the patient that the sample is enriched for prostate-derived tissue or cells. Enrichment for prostate cells may be achieved using, for example, cell sorting methods such as fluorescent activated cell sorting (FACS) using a prostate-selective antibody such as one directed to prostate-specific antigen (PSA). The source of the said sample also includes biopsy material and tumour samples, also including fixed paraffin mounted specimens as well as fresh or frozen tissue.

It will be appreciated that a sample, for example a biopsy sample, may contain more than one cell type, for example it may contain prostate cells, urothelial cells, blood, muscle, fibrocytes, supporting cells and squamous cells. Squamous, urothelial and columnar cells, for example, may be shed into the urine along with prostate cells.

It will be appreciated that quantification of Pax 2 expression may not be informative, for example in some samples containing more than one cell type. It may be sufficient to determine whether Pax 2 expression may be detected in a sample or not, for example using the methods (for example, RT-PCT based methods with detection by ethidium bromide staining) described in example 1, without further quantification. In normal tissue, Pax 2 expression may not be detected, whereas in malignant tissue Pax 2 expression may be detected, using detection methods analagous to those by which expression of the ubiquitous enzyme GAPDH (glyceraldehyde phosphate dehydrogenase) may be detected, for example using the methods described in example 1. Thus, in the methods of the invention a level of Pax 2 nucleic acid or protein associated with prostate cancer may be a level of Pax 2 nucleic acid or protein that may be detected by a method by which Pax 2 nucleic acid or protein is not detected in normal tissue, for example as described in example 1. It will be appreciated that a sample known to contain Pax 2 nucleic acid or protein, for example a previously tested malignant prostate cancer biopsy sample or a sample of a cell line such as UOK 117 (a renal cell carcinoma cell line, which is known to express Pax 2), for example as tested in example 1, may be used as a reference sample. A second reference sample may be a previously tested non-cancerous prostate biopsy sample, for example normal prostate or benign prostatic hyperplasia sample, or sample of a cell line in which Pax 2 has previously not been detectable. As described in example 1, ten benign prostate samples were tested and none expressed Pax 2; thus, a sample of one of these benign prostate samples may be used as a negative control. Further, it appears that no normal adult human cell has been found to express Pax 2; thus it is expected that any normal tissue biopsy sample or non-cancerous cell line may be found not to express Pax 2 and therefore to be suitable as a negative control. U937 cells may be suitable as such a reference negative sample.

It will be appreciated that the methods of the invention may be performed upon one or more individual cells. Thus, the level (which may be the detectable presence/absence) of Pax 2 expression may be assessed in individual cells. The results of the method may be expressed, for example, as a presence of Pax 2 in any of the cells tested, absence of Pax 2 in all of the cells tested, presence of Pax 2 in all of the cells tested, proportion of the cells tested in which the presence of Pax 2 was detected, or a numerical average of the quantified level of Pax 2 across all the cells tested, or across those cells in which Pax 2 expression was detected.

It will be appreciated that the sample in which the presence and/or level of Pax 2 is detected may be a portion of a sample obtained from a patient. For example, the sample in which the presence and/or level of Pax 2 is detected may be one or more cells obtained from a biopsy or urine sample obtained from a patient.

It will be appreciated that determination of the level (which includes determination of presence, in an amount sufficient to be detected, or absence) of the said Pax 2 in the sample will be useful to the clinician in determining how to manage the cancer in the patient. For example, since elevated levels (for example levels which may be detected, as opposed to levels in normal tissue which may be too low to be detected) of the said Pax 2 may be associated with invasiveness or invasive potential, the clinician may use the information concerning the levels or presence of the said Pax 2 to facilitate decision making regarding treatment of the patient. Thus, if the level (for example below the limit of detection) of Pax 2 is indicative of a low invasive potential of said prostate cancer, unnecessary surgery may be avoided. Similarly, if the level (for example a detectable level) of Pax 2 is indicative of a high invasive potential of said prostate cancer, surgery may be the preferred treatment.

It will be appreciated from the foregoing, and from the Examples below, that the determination of the levels (including detectable presence/absence) of the said Pax 2 may be exploited diagnostically to predict whether a given prostate cancer, would invade surrounding tissue or metastasise, since expression of said Pax 2 is believed to correspond to possible future invasion and/or spread of a tumour. Determination of the levels of Pax 2 may be useful in monitoring the recurrence of prostate cancer in patients who have received treatment for prostate cancer, for example treatment which appears to have removed the prostate cancer cells.

It will be appreciated that reference to determining the level of Pax 2 expression includes the meaning of determining whether Pax 2 expression may be detected or not.

It is also particularly preferred if the method of the invention is employed to predict whether a given prostate cancer would invade surrounding tissue.

In one preferred embodiment of the invention it is determined whether the level of said Pax 2 nucleic acid, in particular mRNA, is a level associated with prostate cancer. Preferably, the sample contains nucleic acid, such as mRNA, and the level of said Pax 2 is measured by contacting said nucleic acid with a nucleic acid which hybridises selectively to said Pax 2 nucleic acid.

By "selectively hybridising" is meant that the nucleic acid has sufficient nucleotide sequence similarity with the said human nucleic acid that it can hybridise under moderately or highly stringent conditions, and preferably does not hybridise to other Pax nucleic acids under the same conditions. As is well known in the art, the stringency of nucleic acid hybridization depends on factors such as length of nucleic acid over which hybridisation occurs, degree of identity of the hybridising sequences and on factors such as temperature, ionic strength and CG or AT content of the sequence. Thus, any nucleic acid which is capable of selectively hybridising as said is useful in the practice of the invention.

Nucleic acids which can selectively hybridise to the said human nucleic acid include nucleic acids which have >95% sequence identity, preferably those with >98%, more preferably those with >99% sequence identity, over at least a portion of the nucleic acid with the said human nucleic acid. As is well known, human genes usually contain introns such that, for example, a mRNA or cDNA derived from a gene would not match perfectly along its entire length with the said human genomic DNA but would nevertheless be a nucleic acid capable of selectively hybridising to the said human DNA. Thus, the invention specifically includes nucleic acids which selectively hybridise to said Pax 2 mRNA or cDNA but may not hybridise to a said Pax 2 gene. For example, nucleic acids which span the intron-exon boundaries of the said Pax 2 gene may not be able to selectively hybridise to the said Pax 2 mRNA or cDNA.

Typical moderately or highly stringent hybridisation conditions which lead to selective hybridisation are known in the art, for example those described in *Molecular Cloning, a laboratory manual,* 2nd edition, Sambrook et al (eds), Cold Spring Harbor Laboratory Press, Cold Spring Harbor, N.Y., USA, incorporated herein by reference.

An example of a typical hybridisation solution when a nucleic acid is immobilised on a nylon membrane and the probe nucleic acid is $\geq 500$ bases is:

6×SSC (saline sodium citrate)
0.5% sodium dodecyl sulphate (SDS)
100 μg/ml denatured, fragmented salmon sperm DNA The hybridisation is performed at 68° C. The nylon membrane, with the nucleic acid immobilised, may be washed at 68° C. in 1×SSC or, for high stringency, 0.1×SSC.

20×SSC may be prepared in the following way. Dissolve 175.3 g of NaCl and 88.2 g of sodium citrate in 800 ml of $H_2O$. Adjust the pH to 7.0 with a few drops of a 10 N solution of NaOH. Adjust the volume to 1 liter with $H_2O$. Dispense into aliquots. Sterilise by autoclaving.

An example of a typical hybridisation solution when a nucleic acid is immobilised on a nylon membrane and the probe is an oligonucleotide of between 15 and 50 bases is:

3.0 M trimethylammonium chloride (TMACl)
0.01 M sodium phosphate (pH 6.8)
1 mm EDTA (pH 7.6)
0.5% SDS
100 μg/ml denatured, fragmented salmon sperm DNA
0.1% non-fat dried milk The optimal temperature for hybridization is usually chosen to be 5° C. below the $T_i$ for the given chain length. $T_i$ is the irreversible melting temperature of the hybrid formed between the probe and its target sequence. Jacobs et al (1988) *Nucl. Acids Res.* 16, 4637 discusses the determination of $T_i$s. The recommended hybridization temperature for 17-mers in 3 M TMACl is 48–50° C.; for 19-mers, it is 55–57° C.; and for 20-mers, it is 58–66° C.

By "nucleic acid which selectively hybridises" is also included nucleic acids which may be used to amplify DNA from the Pax 2 cDNA (for example formed by reverse transcription of mRNA) by any of the well known amplification systems such as those described in more detail below, in particular the polymerase chain reaction (PCR).

It is preferred that PCR is used in the methods of the invention.

Suitable conditions for PCR amplification include amplification in a suitable 1×amplification buffer:

10×amplification buffer is 500 mM KCl; 100 mM Tris.Cl (pH 8.3 at room temperature); 15 mM MgCl$_2$; 0.1% gelatin.

A suitable denaturing agent or procedure (such as heating to 95° C.) is used in order to separate the strands of double-stranded DNA.

Suitably, the annealing part of the amplification is between 37° C. and 65° C. The optimum temperature may be 50° C. for most primer pairs, but as discussed in Example 1, a temperature of 60° C. may be preferred for the Pax 2 amplification primers shown below:

Upstream primer: 5' TTTGTGAACGGCCGGCCCCTA 3' (SEQ ID NO:1)

Downstream primer: 5' CATTGTCACAGATGC-CCTCGG 3' (SEQ ID NO:2)

An annealing temperature of 55° C. may be preferred for the GAPDH amplification primers shown below:

Upstream primer: 5' GGCCGTATTGGGCGCCTGGTC 3' (SEQ ID NO:3)

Downstream primer: 5' GAAGGGCAACTACTGTTC-GAAG 3' (SEQ ID NO:4)

These primers may be used in an amplification reaction alongside a reaction using primers, such as those described above, that may amplify nucleic acid encoding part of Pax 2, such that the GAPDH amplification that serves as a positive control for the detection of nucleic acid, as described below, particularly in Example 1.

A temperature of 72° C. may be used for the extension phase of the amplification when a thermostable polymerase is used, such as Taq polymerase.

Although the nucleic acid which is useful in the methods of the invention may be RNA or DNA, DNA is preferred. Although the nucleic acid which is useful in the methods of the invention may be double-stranded or single-stranded, single-stranded nucleic acid is preferred under some circumstances such as in nucleic acid amplification reactions.

The nucleic acid which is useful in the methods of the invention may be any suitable size. However, for certain diagnostic, probing or amplifying purposes, it is preferred if the nucleic acid has fewer than 10 000, more preferably fewer than 1000, more preferably still from 10 to 100, and in further preference from 15 to 30 base pairs (if the nucleic acid is double-stranded) or bases (if the nucleic acid is single stranded). As is described more fully below, single-stranded DNA primers, suitable for use in a polymerase chain reaction, are particularly preferred.

The nucleic acid for use in the methods of the invention is a nucleic acid capable of hybridising to the said Pax 2 mRNAs. Fragments of the said Pax 2 genes and cDNAs derivable from the mRNA encoded by the said Pax 2 genes are also preferred nucleic acids for use in the methods of the invention.

It is particularly preferred if the nucleic acid for use in the methods of the invention is an oligonucleotide primer which can be used to amplify a portion of the said Pax 2 nucleic acid, particularly Pax 2 mRNA. Examples are the primers described above:

Upstream primer: 5' TTTGTGAACGGCCGGCCCCTA 3' (SEQ ID NO:1)

Downstream primer: 5' CATTGTCACAGATGC-CCTCGG 3' (SEQ ID NO:2)

The Pax 2 mRNA is similar to, but distinct from other Pax mRNAs. Preferred nucleic acids for use in the invention are those that selectively hybridise to the Pax 2 mRNA and do not hybridise to other Pax mRNAs.

Such selectively hybridising nucleic acids can be readily obtained, for example, by reference to whether or not they hybridise to the said Pax 2 mRNA or cDNA and not to other Pax mRNAs or cDNAs. The paired box domain is highly conserved, but the carboxy terminal end is variable, so it may be preferred that a selectively hybridising nucleic acid hybridises to a part of a nucleic acid that does not encode the paired box domain, and preferably encodes part of the carboxy terminal region of Pax 2, excluding the paired box domain.

The methods are suitable in respect of any prostate cancer but it is preferred if the cancer is prostate adenocarcinoma. It will be appreciated that other types of prostate cancer may be very rare.

Conveniently, the nucleic acid capable of selectively hybridising to the said human nucleic acid such as mRNA and which is used in the methods of the invention further comprises a detectable label.

By "detectable label" is included any convenient radioactive label such as $^{32}$P, $^{33}$P or $^{35}$S which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Conveniently, the nucleic acid probe may occupy a certain position in a fixed array and whether the nucleic acid hybridises to the said Pax 2 nucleic acid can be determined by reference to the position of hybridisation in the fixed array.

Labelling with [$^{32}$P]dCTP may be carried out using a Rediprime® random primer labelling kit supplied by Amersham.

Primers which are suitable for use in a polymerase chain reaction (PCR; Saiki et al (1988) *Science* 239, 487–491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artefactual product called "primer dimer". When the 3' ends of the two primers hybridise, they form a "primed template" complex, and primer extension results in a short duplex product called "primer dimer".

Internal secondary structure should be avoided in primers. For symmetric PCR, a 40–60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37–55° C. region, so primer extension will occur during the annealing step and the hybrid will be stabilised. The concentrations of the primers are equal in conventional (symmetric) PCR and, typically, within 0.1- to 1-µM range.

It will be appreciated that it may be beneficial to choose primers that will yield different size products from genomic and mRNA-derived templates, for example primers that lie within different exons, so that product amplified from genomic DNA will include one or more intron sequences, whereas product amplified from mRNA-derived template will not include intron sequences.

It will further be appreciated that if a control amplification reaction is to be carried out, for example using primers complementary to an ubiquitously expressed protein, for example GAPDH, that it may be beneficial for the products of the control and Pax 2 derived products to be of different sizes, such that the two products may be distinguished by the detection means employed, for example by mobility on agarose gel electrophoresis. However, it may be desirable for the two products to be of similar size, for example both between 100 and 1000, or between 100 and 600 nucleotides long. This may aid simultaneous analysis of the products, for example by gel electrophoresis, and may also mean that the control and Pax 2 amplification reactions may have similar performance characteristics, in terms, for example, of relative rates of accumulation of product at different stages during the reaction.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991) *Nature* 350, 91–92 and *AIDS* (1993), Vol 7 (Suppl 2), S108 or SDA (strand displacement amplification) can be used as described in Walker et al (1992) *Nucl. Acids Res.* 20, 1691–1696. The polymerase chain reaction is particularly preferred because of its simplicity.

When a pair of suitable nucleic acids of the invention are used in a PCR it is convenient to detect the product by gel electrophoresis and ethidium bromide staining. As an alternative to detecting the product of DNA amplification using agarose gel electrophoresis and ethidium bromide staining of the DNA, it is convenient to use a labelled oligonucleotide capable of hybridising to the amplified DNA as a probe. When the amplification is by a PCR the oligonucleotide probe hybridises to the interprimer sequence as defined by the two primers. The oligonucleotide probe is preferably between 10 and 50 nucleotides long, more preferably between 15 and 30 nucleotides long. It may be longer than the amplified DNA or include one or both of the primers, but in this case, the hybridisation conditions should be such that the probe should not hybridise to the primers alone, but only to an amplified product that also contains interprimer sequence that is capable of hybridising to the probe.

The probe may be labelled with a radionuclide such as $^{32}P$, $^{33}P$ and $^{35}S$ using standard techniques, or may be labelled with a fluorescent dye. When the oligonucleotide probe is fluorescently labelled, the amplified DNA product may be detected in solution (see for example Balaguer et al (1991) "Quantification of DNA sequences obtained by polymerase chain reaction using a bioluminescence adsorbent" *Anal. Biochem.* 195, 105–110 and Dilesare et al (1993) "A high-sensitivity electrochemiluminescence-based detection system for automated PCR product quantitation" *BioTechniques* 15, 152–157.

PCR products can also be detected using a probe which may have a fluorophore-quencher pair or may be attached to a solid support or may have a biotin tag or they may be detected using a combination of a capture probe and a detector probe.

Fluorophore-quencher pairs are particularly suited to quantitative measurements of PCR reactions (eg RT-PCR). Fluorescence polarisation using a suitable probe may also be used to detect PCR products.

Thus, in a preferred method of the invention, total RNA may be prepared from a patient sample or a control sample (as discussed above) using TRIZOL® reagent (Life Technologies™), according to the manufacturers' instructions and 5 µg of total RNA from each sample may be reverse transcribed using a first-strand cDNA synthesis kit (Pharmacia—protocol according to manufacturers' instructions). PCR amplification for Pax 2 cDNA may be performed on the RT product. The ubiquitously expressed GAPDH may be amplified as a control. For amplification of Pax 2 cDNA, the protocol may consist of 35 cycles of denaturation at 95° C., annealing at 60° C. and extension at 72° C. For GAPDH, the annealing temperature may be 55° C. PCR primers may be designed from the published sequence of Pax 2 (see, for example, Sanyanusin et al (1996) *Genomics* 35(1), 258–261; Genbank accession numbers U45245 to U45254). For example, primers used and the size of PCR products may be as follows; Pax 2 (300 base pairs), upstream: 5' TTTGTGAACGGCCGGCCCCTA 3' (SEQ ID NO:1) and downstream: 5' CATTGTCACAGATGC-CCTCGG 3' (SEQ ID NO:2). GAPDH (190 base pairs), upstream: 5'GGCCGTATTGGCGCCTGGTC 3' (SEQ ID NO:5) and downstream 5' GAAGGGCAACTACTGTTC-GAAG 3' (SEQ ID NO:4). Negative controls may be included with water replacing cDNA.

The above primers are designed so that each anneals within an exon, but the amplified fragment crosses boundaries between exons, so that inadvertent amplification of genomic DNA would include an intron. This would easily be identified by the larger size of the fragment on the gel. Positive controls used may be cells known to express Pax 2, for example UOK 117 cells, a renal cell carcinoma cell line.

PCR products may electrophoresed on 1.8% agarose gels and transferred to nylon membranes (Qiabrane Nylon Plus, Qiagen). Filters may hybridised with a human Pax 2 cDNA probe designed from the Pax 2 cDNA sequence, for example the 1.3 kb probe reference 101398 derived from the cDNA sequence from the Max Planck Institut, Goettingen, labeled with [$^{32}P$]dCTP using a Rediprime® random primer labelling kit (Amersham) and ExpressHybe® (Clontech) according to the manufacturer's instructions. The filters may then be exposed to x-ray film. A 20 minute exposure of the filters to the film may be sufficient for detection of the control Pax 2-containing sample and of Pax 2 positive samples, though an overnight exposure is preferred. Control GAPDH-product may be detected in an analogous manner, or by ethidium bromide detection on the gel prior to blotting or on a duplicate gel, as described below.

Alternatively, both Pax 2 and control, for example GAPDH, products may be detected after agarose gel electrophoresis by ethidium bromide staining and UV detection of the products, as well known to those skilled in the art. Ethidium bromide may be added to 100 µg per 100 ml gel (ie 100 µl of 1 mg/ml ethidium bromide solution to 100 ml of agarose solution).

Thus, using the above method, Pax 2 expression may be detected in prostate cancer tissue, particularly from invasive prostate cancer, but may not be detected in normal prostate tissue, whereas GAPDH expression may be detected in prostate cancer and normal prostate tissue.

It will be appreciated that the greater frequency of detection of Pax 2 expression in tumours of higher grade may indicate higher levels of expression of Pax 2 mRNA in tumours of higher grade and therefore a higher probability of the Pax 2 mRNA being amplified to a level at which the amplification product may be detected by the methods described above.

In a further preferred embodiment, the level of said Pax 2 protein is measured. Preferably, the level of said protein is measured by contacting the protein with a molecule which selectively binds to Pax 2.

The sample containing protein derived from the patient is conveniently a sample tissue.

The sample containing protein derived from the patient is conveniently a sample of the tissue in which cancer is suspected or in which cancer may be or has been found. These methods may be used for any prostate cancer. Methods of obtaining suitable samples are described in relation to earlier methods.

The methods of the invention involving detection of the said Pax 2 proteins are particularly useful in relation to historical samples such as those containing paraffin-embedded sections of tumour samples.

The level of said Pax 2 protein may be determined in a sample in any suitable way.

It is particularly preferred if the molecule which selectively binds to Pax 2 is an antibody.

Antibodies which can selectively bind to a particular form of Pax 2 can be made, for example, by using peptides which encompass the differences between Pax 2 and other Pax proteins.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

Polyclonal antibodies to Pax 2 may be obtained from Zymed Company, 20 North Aviador Street, Camarillo, Calif. 93010, USA.

By "the relative amount of said Pax 2 protein" is meant the amount of said Pax 2 protein per unit mass of sample tissue or per unit number of sample cells compared to the amount of said Pax 2 protein per unit mass of known normal tissue or per unit number of normal cells. The relative amount may be determined using any suitable protein quantitation method. In particular, it is preferred if antibodies are used and that the amount of said Pax 2 protein is determined using methods which include quantitative western blotting, enzyme-linked immunosorbent assays (ELISA) or quantitative immunohistochemistry.

Other techniques for raising and purifying antibodies are well known in the art and any such techniques may be chosen to achieve the preparations useful in the methods claimed in this invention. In a preferred embodiment of the invention, antibodies will immunoprecipitate said Pax 2 proteins from solution as well as react with said Pax 2 protein on western or immunoblots of polyacrylamide gels. In another preferred embodiment, antibodies will detect said Pax 2 proteins in paraffin or frozen tissue sections, or in cells recovered from urine samples, using immunocytochemical techniques.

Preferred embodiments relating to methods for detecting said Pax 2 protein include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference. Antibody staining of cells on slides, for example cells recovered from urine samples, may be used, using antibodies to Pax 2 in methods well known in cytology laboratory diagnostic tests, as well known to those skilled in the art.

It will be appreciated that other antibody-like molecules may be used in the method of the inventions including, for example, antibody fragments or derivatives which retain their antigen-binding sites, synthetic antibody-like molecules such as single-chain Fv fragments (ScFv) and domain antibodies (dAbs), and other molecules with antibody-like antigen binding motifs.

In a further embodiment the level of Pax 2 is measured by selectively assaying its activity in the sample. Thus, the binding of Pax 2 to its target DNA sequence may be measured. This may be done using gel-shift assays, for example as described in Adams et al (1992) *Genes & Dev* 6, 1589–1607.

A further aspect of the invention provides use of an agent which is capable of use in determining the level of Pax 2 protein or nucleic acid in a sample in the manufacture of a reagent for diagnosing prostate cancer. The agent may suitably be a nucleic acid which selectively hybridises to Pax 2 nucleic acid or the agent may be a molecule which selectively binds to Pax 2 protein or the agent may be an agent useful in selectively assaying the activity of Pax 2. The agents as defined are therefore useful in a method of diagnosing prostate cancer.

A further aspect of the invention comprises a kit of parts useful for diagnosing prostate cancer, comprising an agent which is capable of use in determining the level of Pax 2 protein or nucleic acid in a sample. The agent may be a nucleic acid which selectively hybridises to Pax 2 nucleic acid or the agent may be a molecule which selectively binds to Pax 2 protein or the agent may be an agent useful in selectively assaying the activity of Pax 2.

Preferably, the kit further comprises a control sample containing Pax 2 nucleic acid or protein wherein the control sample may be a negative control (which contains a level of Pax 2 protein or nucleic acid which is not associated with prostate cancer or a high invasive potential for prostate cancer, for example a level of Pax 2 protein or nucleic acid which is not detectable) or it may be a positive control (which contains a level of Pax 2 protein or nucleic acid which is associated with prostate cancer or a high invasive potential for prostate cancer, for example a level that may be detected). The kit may contain both negative and positive controls. The kit may usefully contain controls of Pax 2 protein or nucleic acid which correspond to different amounts such that a calibration curve may be made.

A further aspect of the invention provides a method of treating prostate cancer comprising the step of administering to the patient an agent which selectively prevents the function of Pax 2.

By "an agent which selectively prevents the function of Pax 2" we include agents that (a) inhibit the expression of said Pax 2 or (b) inhibit the activity of said Pax 2.

Agents that prevent the expression of said Pax 2 include but are not limited to antisense agents. An example of an antisense agent is an antisense oligonucleotide that has been used in renal cancer cell lines and rhabdomyosarcoma cell (Gnarra & Dressler (1995) *Cancer Res* 55, 4092–4098; Bernasconi et al (1996) *PNAS* 93(23), 13164–13169). Retinoic acid may inhibit Pax 2.

Antisense oligonucleotides are single-stranded nucleic acid, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A)addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci. (USA)* 85(15), 5507–11). The Goodchild study showed that oligonucleotides that were most effective were complementary to the poly(A) signal; also effective were those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079–7083 showed increased inhibition in tissue culture of HIV-1 using oligonucleotide phosphoramidates and phosphorothioates. Sarin et al (1988) *Proc. Natl. Acad. Sci. USA* 85, 7448–7451 demonstrated increased inhibition of HIV-1 using oligonucleotide methylphosphonates. Agrawal et al (1989) *Proc. Natl. Acad. Sci. USA* 86, 7790–7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430–3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res.* 19, 747–750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesising oligonucleoside phosphorothioates is provided in Agrawal and Tang (1990) *Tetrahedron Letters* 31, 7541–7544, the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) *Tetrahedron Letters* 28, 3401; Bannwarth (1988) *Helv. Chim. Acta.* 71, 1517; Crosstick and Vyle (1989) *Tetrahedron Letters* 30, 4693; Agrawal et al (1990) *Proc. Natl. Acad. Sci. USA* 87, 1401–1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesised and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747–750 and Agrawal et al (1991) *Proc. Natl. Acad. Sci. USA* 88(17), 7595–7599, the teachings of which are hereby incorporated herein by reference.

A further method of making oligonucleotides resistant to nuclease attack is for them to be "self-stabilised" as described by Tang et al (1993) *Nucl. Acids Res.* 21, 2729–2735 incorporated herein by reference. Self-stabilised oligonucleotides have hairpin loop structures at their 3' ends, and show increased resistance to degradation by snake venom phosphodiesterase, DNA polymerase I and fetal bovine serum. The self-stabilised region of the oligonucleotide does not interfere in hybridization with complementary nucleic acids, and pharmacokinetic and stability studies in mice have shown increased in vivo persistence of self-stabilised oligonucleotides with respect to their linear counterparts.

It is preferred that the antisense reagent is able to bind to Pax 2 nucleic acid, but not nucleic acid encoding any other Pax protein. It may therefore be preferred that the antisense reagent does not hybridise to the region of the Pax 2 nucleic acid encoding the paired box domain, but may hybridise to the carboxy terminal region of Pax 2.

In accordance with the invention, the antisense compound may be administered systemically. Alternatively, the inherent binding specificity of antisense oligonucleotides characteristic of base pairing may be enhanced by limiting the availability of the antisense compound to its intended locus in vivo, permitting lower dosages to be used and minimising systemic effects. Thus, oligonucleotides may be applied locally to achieve the desired effect. The concentration of the oligonucleotides at the desired locus is much higher than if the oligonucleotides were administered systemically, and the therapeutic effect can be achieved using a significantly lower total amount. The local high concentration of oligonucleotides enhances penetration of the targeted cells and effectively blocks translation of the target nucleic acid sequences.

The oligonucleotides can be delivered to the locus by any means appropriate for localised administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus. Oligonucleotides may be delivered directly to the gland via the transrectal or trans-perineal route, as well known to those skilled in the art.

The oligonucleotides may be administered via a hydrogel material. The hydrogel is noninflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10 to about 80% by weight ethylene oxide and from about 20 to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warms, it solidifies to form a gel, and the oligonucleotides diffuse out of the gel into the surrounding cells over a period of time defined by the exact composition of the gel.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerized or solidified, using melt or solvent evaporation techniques, or mechanically mixed with the material. In one embodiment, the oligonucleotides are mixed into or applied onto coatings for implantable devices such as dextran coated silica beads, stents, or catheters. Polymeric nanoparticles/biodegradable drug carriers may also be used (Mader (1998) *Radiol. Oncol.* 32, 89–94).

The dose of oligonucleotides is dependent on the size of the oligonucleotides and the purpose for which is it administered. In general, the range is calculated based on the surface area of tissue to be treated. The effective dose of oligonucleotide is somewhat dependent on the length and chemical composition of the oligonucleotide but is generally in the range of about 30 to 3000 µg per square centimeter of tissue surface area.

The oligonucleotides may be administered to the patient systemically for both therapeutic and prophylactic purposes. The oligonucleotides may be administered by any effective method, for example, parenterally (eg intravenously, subcutaneously, intramuscularly) or by oral, nasal or other means which permit the oligonucleotides to access and circulate in the patient's bloodstream. Oligonucleotides administered systemically preferably are given in addition to locally administered oligonucleotides, but also have utility in the absence of local administration. A dosage in the range of from about 0.1 to about 10 grams per administration to an adult human generally will be effective for this purpose.

It will be appreciated that it may be desirable to target the antisense oligonucleotides to the prostate. This may be achieved by administering the antisense oligonucleotides to the prostate, or it may be achieved by using antisense oligonucleotides which are in association with a molecule which selectively directs the antisense oligonucleotide to the prostate. For example, the antisense oligonucleotide may be associated with an antibody or antibody like molecule which selectively binds a prostate-related antigen such as PSA. By "associated with" we mean that the antisense oligonucleotide and the prostate-directing entity are so associated that the prostate-directing entity is able to direct the antisense oligonucleotide to the prostate cells.

It will be appreciated that the oligonucleotides or other agents may be administered after surgical removal of a tumour, and may be administered to the area from which the tumour has been removed, and surrounding tissue, for example using cytoscopy to guide application of the oligonucleotides or other agents.

It will be appreciated that antisense agents also include larger molecules which bind to said Pax 2 mRNA or genes and substantially prevent expression of said Pax 2 mRNA or genes and substantially prevent expression of said Pax 2 protein. Thus, expression of an antisense molecule which is substantially complementary to said Pax 2 mRNA is envisaged as part of the invention.

As discussed above, it is preferred that the antisense molecule is not able to substantially prevent expression of other Pax mRNAs or proteins. It may therefore preferably not be complementary solely to the region of the Pax 2 mRNA that encodes the paired box domain, and is more preferably not complementary to the region of the Pax 2 mRNA that encodes the paired box domain.

The said larger molecules may be expressed from any suitable genetic construct as is described below and delivered to the patient. Typically, the genetic construct which expresses the antisense molecule comprises at least a portion of the said Pax 2 cDNA or gene operatively linked to a promoter which can express the antisense molecule in the cell, preferably prostate cell, which is or may become cancerous. Promoters that may be active in prostate cells or cancerous prostate cells will be known to those skilled in the art, and may include promoters for ubiquitously expressed, for example housekeeping genes.

It will be appreciated that it may be desirable that the antisense molecule or ribozyme is expressed from a prostate cell-specific promoter element. Prostate-specific antigen (PSA) is one of the major protein constituents of the human prostate secretion. It has become a useful marker for the detection and monitoring of prostate cancer. The gene encoding PSA and its promoter region which directs the prostate-specific expression of PSA have been described (Lundwall (1989) *Biochem. Biophys. Res. Comm.* 161, 1151–1159; Riegman et al (1989) *Biochem. Biophys. Res. Comm.* 159, 95–102; Brawer (1991) *Acta Oncol.* 30, 161–168). Thus, suitably, the promoter is the PSA promoter.

Although the genetic construct can be DNA or RNA it is preferred if it is DNA.

Preferably, the genetic construct is adapted for delivery to a human cell.

Means and methods of introducing a genetic construct into a cell in an animal body are known in the art. For example, the constructs of the invention may be introduced into the tumour cells by any convenient method, for example methods involving retroviruses, so that the construct is inserted into the genome of the tumour cell. For example, in Kuriyama et al (1991) *Cell Struc. and Func.* 16, 503–510 purified retroviruses are administered. Retroviruses provide a potential means of selectively infecting cancer cells because they can only integrate into the genome of dividing cells; most normal cells surrounding cancers are in a quiescent, non-receptive stage of cell growth or, at least, are dividing much less rapidly than the tumour cells. Retroviral DNA constructs which encode said antisense agents may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a neo$^R$ gene). Independent colonies are isolated and expanded and the culture supernatant removed, filtered through a 0.45 μm pore-size filter and stored at −70°. For the introduction of the retrovirus into the tumour cells, it is convenient to inject directly retroviral supernatant to which 10 μg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992) *Science* 256, 1550–1552, cells which produce retroviruses are injected into the tumour. The retrovirus-producing cells so introduced are engineered to actively produce retroviral vector particles so that continuous productions of the vector occurred within the tumour mass in situ. Thus, proliferating tumour cells can be successfully transduced in vivo if mixed with retroviral vector-producing cells.

Targeted retroviruses are also available for use in the invention; for example, sequences conferring specific binding affinities may be engineered into preexisting viral env genes (see Miller & Vile (1995) *Faseb J.* 9, 190–199 for a review of this and other targeted vectors for gene therapy).

Other methods involve simple delivery of the construct into the cell for expression therein either for a limited time or, following integration into the genome, for a longer time. An example of the latter approach includes (preferably tumour-cell-targeted) liposomes (Nässander et al (1992) *Cancer Res.* 52, 646–653).

Immunoliposomes (antibody-directed liposomes) are especially useful in targeting to cancer cell types which over-express a cell surface protein for which antibodies are available. For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286–288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 μm and 0.2 μm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected intraperitoneally or directly into the tumour.

Other methods of delivery include adenoviruses carrying external DNA via an antibody-polylysine bridge (see Curiel *Prog. Med. Virol.* 40, 1–18) and transferrin-polycation conjugates as carriers (Wagner et al (1990) *Proc. Natl. Acad. Sci. USA* 87, 3410–3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalised into the cell and carries into the cell with it the DNA construct of the invention. It is preferred if the polycation is polylysine.

The DNA may also be delivered by adenovirus wherein it is present within the adenovirus particle, for example, as described below.

In the second of these methods, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) Proc. Nat. Acad. Sci. USA 89, 6094–6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It may be desirable to locally perfuse a tumour with the suitable delivery vehicle comprising the genetic construct for a period of time; additionally or alternatively the delivery vehicle or genetic construct can be injected directly into accessible tumours.

It will be appreciated that "naked DNA" and DNA complexed with cationic and neutral lipids may also be useful in introducing the DNA of the invention into cells of the patient to be treated. Non-viral approaches to gene therapy are described in Ledley (1995) Human Gene Therapy 6, 1129–1144.

Alternative targeted delivery systems are also known such as the modified adenovirus system described in WO 94/10323 wherein, typically, the DNA is carried within the adenovirus, or adenovirus-like, particle. Michael et al (1995) Gene Therapy 2, 660–668 describes modification of adenovirus to add a cell-selective moiety into a fibre protein. Mutant adenoviruses which replicate selectively in p53-deficient human tumour cells, such as those described in Bischoff et al (1996) Science 274, 373–376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

In a further embodiment the agent which selectively prevents the function of Pax 2 is a ribozyme capable of cleaving targeted Pax 2 RNA or DNA. A gene expressing said ribozyme may be administered in substantially the same way and using substantially the same vehicles as for the antisense molecules.

Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149,796; Cech et al "RNA ribozyme restriction endoribonucleases and methods", U.S. Pat. No. 5,116, 742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

It will be appreciated that it may be desirable that the antisense molecule or ribozyme is expressed from a prostate cell-specific promoter element.

The genetic constructs of the invention can be prepared using methods well known in the art.

A variety of methods have been developed to operably link DNA to vectors via complementary cohesive termin. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as well know to those skilled in the art, is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) Science 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The present invention also relates to a host cell transformed with a genetic (preferably DNA construct) construct of the present invention. The host cell can be either prokaryotic or eukaryotic. Bacterial cells are preferred prokaryotic host cells and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) *Mol. Microbiol.* 2, 637–646 incorporated herein by reference. The greatest number of transformants is consistently recovered following electroporation of the DNA-cell mixture suspended in 2.5×PEB using 6250V per cm at 25 $\mu$FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the cytotoxic gene product as defined in the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

When the genetic construct is a plasmid DNA construct it can be purified. The DNA construct of the invention is purified from the host cell using well known methods.

For example, plasmid vector DNA can be prepared on a large scale from cleaved lysates by banding in a CsCl gradient according to the methods of Clewell & Helinski (1970) *Biochemistry* 9, 4428–4440 and Clewell (1972) *J. Bacteriol.* 110, 667–676. Plasmid DNA extracted in this way can be freed from CsCl by dialysis against sterile, pyrogen-free buffer through Visking tubing or by size-exclusion chromatography.

Alternatively, plasmid DNA may be purified from cleared lysates using ion-exchange chromatography, for example those supplied by Qiagen. Hydroxyapatite column chromatography may also be used.

In an embodiment of the invention, anti-Pax 2 antibodies (Pax 2-Abs) conjugated with a dye substance are applied to the prostate gland in vivo (eg Yasmuch et al (1993) "Antibody targeted photolysis" *Critical Review Revue Ther. Drug Carrier System* 10, 197–252; Pogrebniak et al (1993) "Targetted phototherapy with sensitizer-monoclonal antibody conjugate and light" *Surgical Onoclogy* 2, 31–42). The gland is then irradiated locally with a wavelength of light/ laser matching the absorption peak of the 'attached' dye. Absorption of the light energy by the dye leads to local heating and cell death. In this way, only the labelled (ie metastatic) cells will be ablated. Pax 2-Abs labelled with the following dyes may be used: fluorescein (Pelegrin et al (1991) "Antibody fluorescein conjugates for photoimmuno-diagnosis of human colon-carcinoma in nude-mice" *Cancer* 67, 2529–2537); rhodamine (Haghighat et al (1992) "Laser-dyes for experimental phototherapy of human cancer— comparison of 3 rhodamines" *Laryngoscope* 102, 81–87); cyanins (Folli et al (1994) "Antibody-indocyanin conjugates for immunophotodetection of human squamous-cell carcinoma in nude-mice" *Cancer Research* 54, 2643–2649; Lipshutz et al (1994) "Evaluation of 4 new carbocyanine dyes for photodynamic therapy with lasers" *Laryngoscope* 104, 996–1002; Haddad et al (1998) "In vitro and in vivo effects of photodynamic therapy on murine malignant melanoma" *Annals of Surgical Oncology* 5, 241–247).

A further aspect of the invention is a method of identifying a suppressor gene or an activator gene for Pax 2 wherein a nucleic acid corresponding to known deletions or duplications in prostate cancer or the product of transcription and/or translation of said nucleic acid is tested to determine whether it may selectively prevent or enhance the function of Pax 2. Thus, the nucleic acid or product may be tested to determine whether it alters the transcription or translation of Pax 2, or affects the stability of Pax 2, or to determine whether it prevents or enhances the binding of Pax 2 to its target DNA. Preferably, the effect on transcription, translation or stability is tested.

A further aspect of the invention provides use of an agent which selectively prevents the function of Pax 2 in the manufacture of a medicament for treating prostate cancer.

A still further aspect of the invention provides a genetic construct comprising a nucleic acid encoding a molecule capable of preventing the function of Pax 2 expressed in a prostate cell.

As noted above, the genetic construct may be RNA or DNA. The molecule capable of preventing the function of Pax 2 is conveniently an antisense molecule or a ribozyme as disclosed above.

The genetic constructs are adapted for delivery to a human cell, in particular a cell which is cancerous or in which cancer may occur, and more particularly the genetic construct is adapted for delivery to a prostate cell. The genetic constructs of this aspect of the invention include the viral and non-viral delivery systems described above.

Suitably, the molecule is capable of preventing the function of Pax 2, such as a ribozyme or antisense molecule, is selectively expressed in a prostate cancer cell. For example, expression of said molecule by the genetic construct may be via a prostate cancer cell- or tissue-selective promoter which may be a prostate cell-selective promoter, for example the PSA promoter or any other prostate-selective promoter as discussed above.

A further aspect of the invention provides the genetic constructs for use in medicine. Thus, the genetic constructs are packaged and presented for use in medicine.

A further aspect of the invention provides a pharmaceutical composition comprising a genetic construct of the invention and a pharmaceutically acceptable carrier. The carriers must be "acceptable" in the sense of being compatible with the genetic construct of the invention and not deleterious to the recipients thereof. Typically, the carriers will be water or saline which will be sterile and pyrogen free.

For the avoidance of doubt, the genetic constructs of the invention specifically include virus or virus-like particles.

The invention will now be described by reference to the following Examples and Figures:

FIG. 1.

a) Pax 2 expression in channel TURP (transurethral resection of the prostate) specimens. The specimens are from patients who are known to have metastatic prostate cancer from a previous biopsy. The patients have been on anti-androgen treatment and the transurethral resection of the prostate is done to alleviate symptoms. Gel electrophoresis of RTPCR products shows a 300 base pair PCR product in three of the five specimens examined, visualised by Southern transfer, hybridisation to Pax 2 and autoradiography as described in the Materials and Method section. OUK 117 cells were used as the positive control.

b) GAPDH expression in the same specimens examined by RTPCR. Gel electrophoresis of RTPCR for GAPDH (200 base pair fragment) shows expression in all of the specimens when visualised with ethidium bromide staining.

FIG. 2.

a) Pax 2 expression in ten benign prostatic hypertrophy specimens examined by RTPCR. Gel electrophoresis of RTPCR, for Pax 2 (300 base pair fragment), shows expression in none of the benign prostatic hypertrophy specimens examined when visualised with ethidium bromide staining. A band is present in the positive control lane.

b) GAPDH expression in the same specimens examined by RTPCR. Gel electrophoresis of RTPCR for GAPDH (200 base pair fragment) shows expression in all of the specimens when visualised with ethidium bromide staining.

FIG. 3.

a) Pax 2 expression in cell lines. LNCaP, DU145 and PC3 are established prostate cancer cell lines. Gel electrophoresis of RTPCR products shows a 300 base pair PCR product in the samples from each of the cell lines, visualised by Southern transfer, hybridisation to Pax 2 and autoradiography as described in the Materials and Method section. UOK 117 and UOK 231 cells were used as the positive control.

b) GAPDH expression in the same specimens examined by RTPCR. Gel electrophoresis of RTPCR for GAPDH (200 base pair fragment) shows expression in all of the specimens when visualised with ethidium bromide staining.

FIG. 4.

a) and b) Pax 2 expression in fifteen radical prostatectomy specimens examined by RTPCR. Gel electrophoresis of RTPCR, for Pax 2 (300 base pair fragment), shows expression in ten of the radical prostatectomy specimens examined when visualised with ethidium bromide staining. A band is present in the positive control lane and in the lanes corresponding to specimens 1, 3, 19, 21, 24, 27, 32, 38, 41 and 43. Bands may also be present in the lanes corresponding to specimens 25 and 26.

c) GAPDH expression in the same specimens examined by RTPCR. Gel electrophoresis of RTPCR for GAPDH (200 base pair fragment) shows expression in all of the specimens when visualised with ethidium bromide staining. The gel shown is of RTPCR for GAPDH on specimens 24, 27, 32, 38, 41 and 43.

FIG. 5A. Lack of PAX2 expression in non-malignant prostate specimens by RT-PCR

UOK-117 was used as positive control. Water was substituted for DNA in the negative controls. The expected band sizes for the PAX2 genomic and cDNA PCR products are shown by arrows.

A1. Gel electrophoresis showing no PAX2 expression in five normal prostate (N1 to N5).

A2. The Southern hybridisation of a blot from gel A1 with the PAX2 probe, confirming the results.

FIG. 5A3. Shows PAX2 expression on 27 prostate cancers using RT-PCR and Southern blotting B1. RT-PCR products are size separated on 1.0% agarose gel. No PAX2 expression is detected in 10 BPH samples (T1 to T10). Genomic PAX2 is amplified.

B2. The results in B1 are confirmed by Southern hybridisation.

Figure 5B:
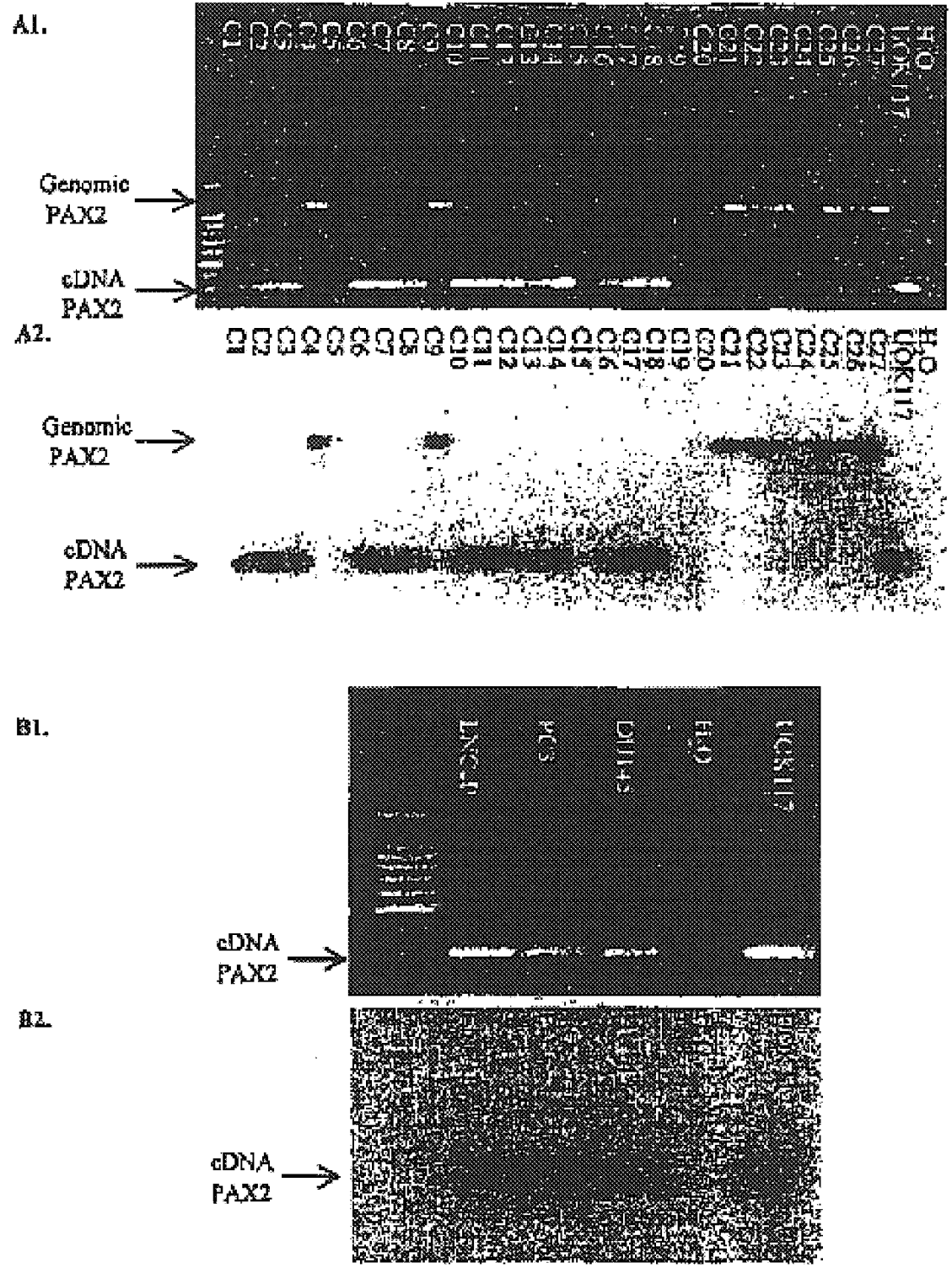

FIG. 5B. PAX2 expression in prostate cancer specimens and cell lines by RT-DCR

UOK-117 was used as a positive control. DNA was replaced with water for the negative control. The genomic and cDNA PAX2 expected band sizes are shown by arrows.

A1. Gel electrophoresis of the products of RT-PCR for PAX2 on prostate cancer specimens (C1–C27). 14 out of 27 cancers express PAX2.

A2. The Southern hybridisation of a blot from gel A1 to the PAX2 probe (1398).

B1. PAX2 expression was detected in all 3 prostate cancer cell lines. B2. The expression of PAX2 is confirmed by Southern hybridisation of a blot from gel B1 to PAX2 probe (1398).

Figure 5C:
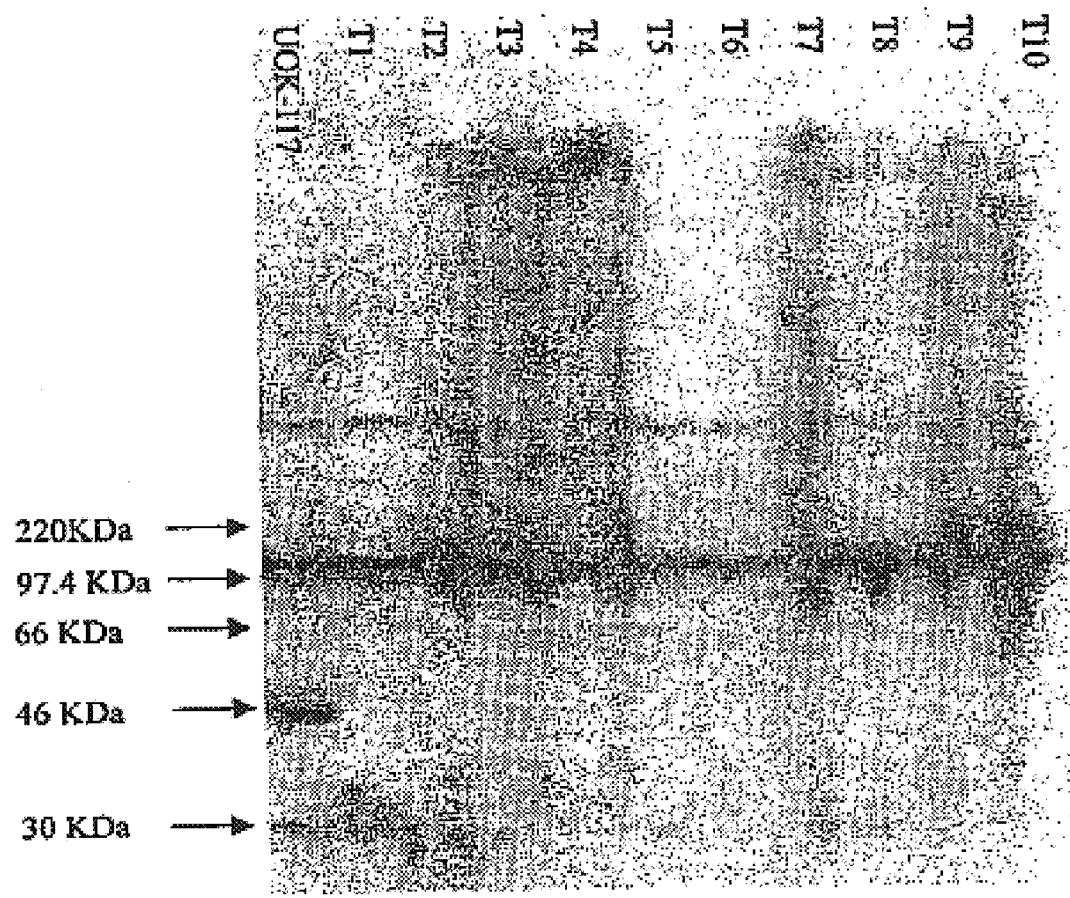

FIG. 5C. Lack of PAX2 protein expression in benign prostatic hypertrophy samples using Western blotting UOK117 is used as a positive control. Using the primary antibody (polyclonal anti-rabbit PAX2 IgG from Zymed) PAX2 produces a double band (46 and 48 KDa). As shown, none of the benign samples express PAX2. Due to the primary being a polyclonal there is some non-specific staining which is present in all samples including the positive control.

Figure 5D:
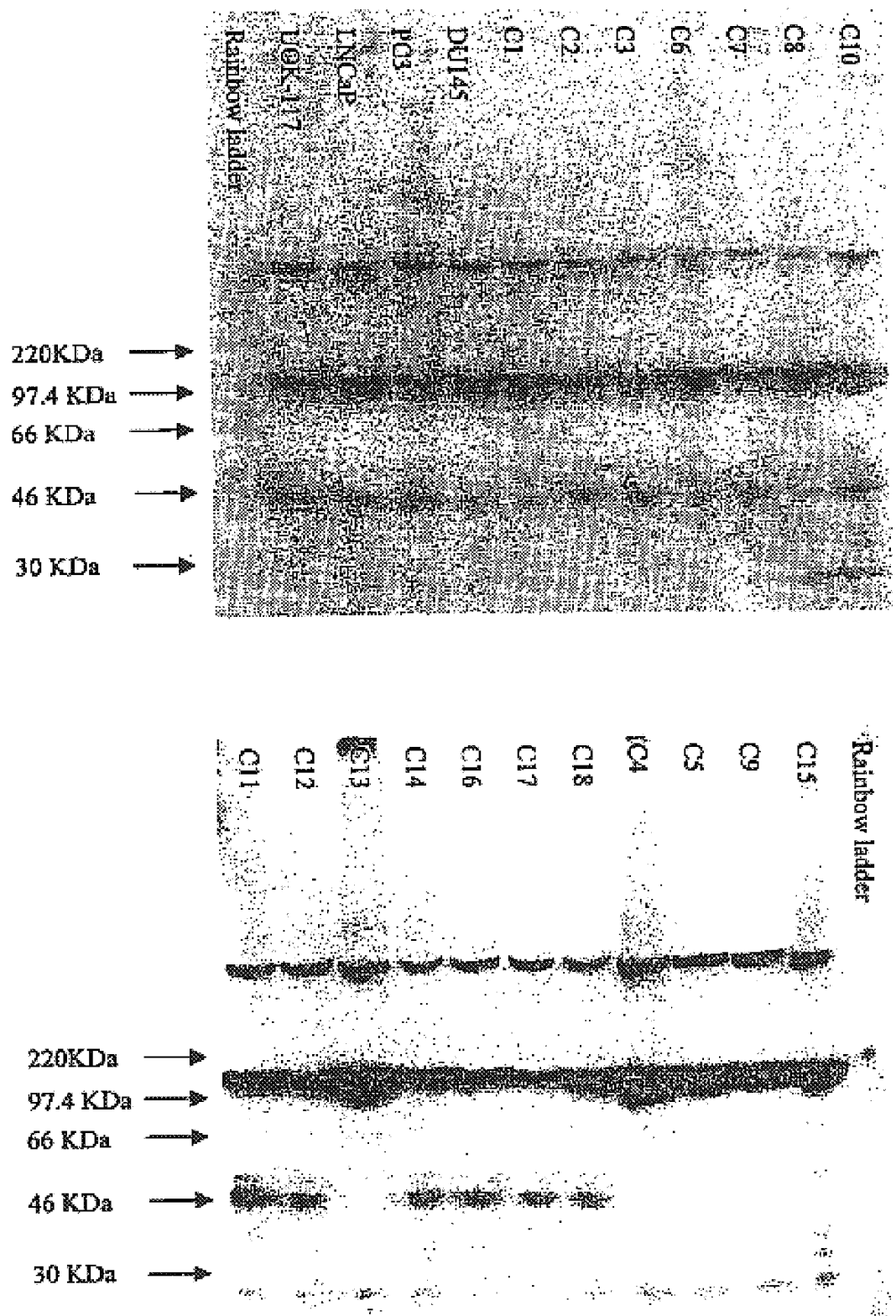

FIG. 5D. PAX2 protein is expressed in 13 out of the 14 prostatic cancers that expressed PAX2 mRNA (FIG. 5B)

UOK117 was used as positive control. PAX2 gives a double band at 46 and 48 Kda. All three prostate cancer cell lines express PAX2 protein. Out of the 14 prostate cancers that showed PAX2 expression by RT-PCR, PAX2 protein expression was detected in 13 of them. Prostate cancers C4, C5, C9 and C15 did not express PAX2 protein or mRNA (FIG. 5B). The non-specific staining was present in all samples.

EXAMPLE 1

The Expression of Pax 2 in Prostate Cancer

Three established prostate cancer cell lines, specimens from five known adenocarcinomas of the prostate and from ten benign prostatic hyperplasias were investigated using reverse transcription polymerase chain reaction to detect Pax 2 expression. We show here that Pax 2 is expressed in the cancer cell lines and in three out of five of the known adenocarcinoma of the prostate specimens, but not in the benign prostatic hyperplasia samples. Pax 2 may therefore be an important diagnostic marker of prostate cancer.

Normal development requires transcription of specific genes in an ordered temporal and spatial manner. This regulated cell growth is in sharp contrast to the deregulated cell growth involved in oncogenesis. This relationship has led to the discovery of a novel mechanism of oncogenesis. Inappropriate or deregulated expression of developmental genes has been shown to play a role in several tumours (Stuart E T et al PAX and HOX in neoplasia. Advances in Genetics 1995;33(255):255–74).

The family of nine Pax genes encode nuclear transcription factors and are highly influential in controlling embryonic development. They all contain a "paired box" region of 384 base pairs encoding a DNA binding domain which is highly conserved throughout evolution (Stuart E T et al Mammalian Pax genes. Annual Review of Genetics 1994;28(219):219–36). The influence of Pax genes on developmental processes has been demonstrated by the numerous natural mouse and human syndromes that can be attributed directly to even a heterozygous insufficiency in a Pax gene (Busslinger M, Urbanek P. The role of BSAP (Pax-5) in B-cell development. Current Opinion in Genetics & Development 1995;5(5):595–601.

The sub-group of Pax 2,5 and 8 (Class III) are expressed latest in development and only in undifferentiated, highly mitotic cells of the ventricular zone of the CNS (Pax 2, 5 and 8), the developing kidney (Pax 2 & 8), B-cell progenitors (Pax 5) and the thyroid (Pax 8). In mice, after birth, Pax 5 is expressed exclusively in B cells and testis (Busslinger M, Urbanek P. The role of BSAP (Pax-5) in B-cell development. Current Opinion in Genetics & Development 1995;5(5):595–601. These transcription factors are prime candidates for proto-oncogenes because of their powerful effect on cellular growth and differentiation and the salient feature of expression of Pax 2,5 and 8 in highly mitotic, undifferentiated cells. Pax genes are capable of transforming fibroblasts and producing solid, vascular tumours in nude mice (Maulbecker C C, Gruss P. The oncogenetic potential of Pax genes. Embo J 1993;12(6):2361–7). They have also been shown to be expressed inappropriately in a number of different human tumours eg glioblastoma (Pax 5), renal cell carcinoma (Pax 2), medulloblastoma, non-Hodgkins lymphoma (Pax 5), Wilms tumour (Pax 2 and 8) and rhabdomyosarcoma (Pax 3 and 7) (reviewed in Stuart E T, Yokota Y, Gruss P. PAX and HOX in neoplasia. Advances in Genetics 1995;33(255):255–74).

Cytogenetic and allele loss studies have pointed to a number of chromosomal regions of potential involvement in prostate cancer. Cannon-Albright & Eeles (1995) *Nature Genetics* 9, 336–338 discuss candidate regions for tumour suppressor prostate cancer susceptibility loci from loss-of-heterozygosity (LOH) studies which occur on human chromosome regions 3p, 7q, 8p, 9q, 10p, 10q, 11p, 13q, 16q, 17p, 18q and Y; whereas Brothman et al (1990) *Cancer Res.* 50 3795–3803 surveyed cytogenetic information on human prostate adenocarcinoma which indicated loss of chromosomes 1, 2, 5 and Y and gain of 7, 14, 20 and 22, with rearrangements involving chromosome arms 2p, 7q and 10q being most common. Studies by Gao et al (1994) *Oncogene* 9, 2999–3003 indicate that a positive mutator phenotype in at least one of chromosomes 3p, 5q, 6p, 7p, 8p, 10q, 11p, 13q, 16q, 17p, 18q and Xq is found in prostate adenocarcinoma; and Massenkeil et al (1994) *Anticancer Res.* 14(6B), 2785–2790 indicates that LOH was observed at 8p, 17p, 18q in various prostate tumour samples but no deletions were observed on 10q in fourteen informative prostate tumours. Zenklusen et al (1994) *Cancer Res.* 54, 6370–6373 suggests that there is a possible tumour suppressor gene at 7q31.1. In addition, there have been other reports which describe other chromosome loss or abnormalities. Nihei et al (1995) *Genes, Chromosomes & Cancer* 14, 112–119, for example, describes the localization of a metastasis suppressor gene for rat prostatic cancer.

Thus, loss of, or abberations in, most human chromosomes has been implicated in prostate cancer by one research group or another.

A number of tumours exhibit precise loss of the region 10q23-q25 (2, 3), suggesting the presence of a tumour suppressor gene in this area. Mxi1, which encodes a negative regulator of the Myc oncoprotein and resides at 10q25, has been proposed as a candidate for the tumour suppressor gene (4). WO97/15686 describes the identification of a prostate tumour suppressor gene near the 10q23-q24 boundary that is distinct from Mxi1. Li et al (1997) *Science* 275, 1943–1947 and Steck et al (1997) *Nature Genet* 15, 356–362 report the identification of the same gene, named PTEN or MMAC1.

The human Pax 2 gene is located on chromosome 10 at 10q25. As described above, chromosome 10q has been implicated in prostate cancer.

During development, Pax 5 is expressed in the early stages of B cell development but is downregulated rapidly before terminal differentiation: similarly, Pax 2 and 8 are downregulated after the transition from mesenchmye to epithelium during renal development (Phelps D E, Dressler G R. Aberrant expression of Pax-2 in Danforth's short tail (Sd)mice. Developmental Biology 1993; 157(1):251–8). It is interesting to speculate that expression of Pax 2 seen in prostate tumours might represent a "reverse mechanism" to that seen in development ie that it is required in order for a terminally differentiated cell to dedifferentiate and adopt a neoplastic phenotype. Constitutive expression of Pax 2, 5 and 8 would keep a cell in an undifferentiated state, thus contributing to its oncogenic potential. It has been shown that constitutive expression of Pax 2 in mice, under the control of a CMV promoter, blocks terminal differentiation and the pathological state resembles precancerous lesions (Dressler G R et al Deregulation of Pax 2 expression in transgenic mice generates severe kidney abnormalities. Nature 362:65–67).

In renal cell carcinoma, it was shown that 73% of tumours studied expressed Pax 2 mRNA and protein and that treatment with antisense oligodeoxynucleotides not only downregulated the protein but produced a considerable growth inhibition in culture (Gnarra J R, Dressler G R. Expression of Pax-2 in human renal cell carcinoma and growth inhibition by antisense oligonucleotides. Cancer Research 1995; 55(18):4092–8).

An important inverse relationship between Pax 5-expressing astrocytomas and p53 expression led to the discovery that Pax 2, 5 and 8 proteins are capable of binding to a sequence within the 5' regulatory region of the human p53 gene and repressing its activity (Stuart E T et al. Loss of p53 function through PAX-mediated transcriptional repression. Embo Journal 1995;14(22):5638–45). This novel, proposed mechanism for down-regulation of the p53 tumour supressor gene without the need for mutation is a possible mechanism for the action of Pax 2 in prostate cancer.

Pax 2 has an important role in the pathogenesis of Wilms tumour and renal cell carcinoma and is transcriptionally repressed by the Wilms tumour supressor gene (Ryan G, Steele P V, Morris J F, Rauscher F, Dressler G R. Repression of Pax-2 by WT1 during normal kidney development. Development 1995;121(3):867–75). It is therefore possible that the loss of a tumour supressor gene as yet unidentified in prostate cancer could account for the deregulated expression of Pax 2.

Materials and Methods

Cell Lines and Primary Tumour

Three established cell lines LNCaP, DU145 and PC3 were obtained from St George's Hospital and are also available from the American Type Culture Collection (ATCC). The cells were cultured in DMEM with 10% FCS and antibiotics. Five prostate cancer samples were obtained from patients known to have metastatic prostate cancer from a previous transrectal biopsy. The patients had been on anti-androgen treatment and the samples were obtained by transurethral resection of the prostate, done in order to alleviate symptoms. The samples were collected directly from the operating theatre, frozen in liquid nitrogen and stored at −70° C. until RNA extraction. Frozen sections of the sample were examined by a pathologist in order to reconfirm the diagnosis. The gleason scores for these samples are shown in Table 1. Benign prostatic hyperplasia samples were obtained in a similar manner from patients who had been diagnosed as having benign prostatic hyperplasia. The benign nature of the specimens was confirmed by histological examination of frozen sections, as for the prostate cancer samples. Fifteen radical prostatectomy specimens were obtained from patients with prostate cancer diagnosed on biopsy.

PCR Amplification of Pax 2 cDNA

Total RNA was prepared using TRIZOL® reagent (Life Technologies™), according to the manufacturers' instructions and in each case 5 μg of total RNA was reverse transcribed using a first-strand cDNA synthesis kit (Pharmacia—protocol according to manufacturers' instructions). PCR amplification for Pax 2 cDNA was performed on the RT product. The ubiquitiously expressed GAPDH was amplified as a control. For amplification of Pax 2 cDNA, the protocol used consisted of 35 cycles of denaturation at 95° C., annealing at 60° C. and extension at 72° C. For GAPDH, the annealing temperature was reduced to 55° C. Primers used and the size of PCR products were as follows; Pax 2 (301 base pairs), upstream: 5' TTTGT-GAACGGCCGGCCCCTA 3' (SEQ ID NO:1) and downstream: 5' CATTGTCACAGATGCCCTCGG 3' (SEQ ID NO:2). GAPDH (190 base pairs), upstream: 5' GGCCG-TATTGGCGCCTGGTC 3' (SEQ ID NO:5) and downstream 5' GAAGGGCAACTACTGTTCGAAG 3' (SEQ ID NO:4). Negative controls were included with water replacing cDNA.

All the-primers were designed so that each annealed within an axon, but the amplified fragment crossed boundaries between exons, so that inadvertent amplification of genomic DNA would include an intron. This would easily be identified by the larger size of the fragment on the gel. Positive controls used were UOK231 and UOK117 cells known to express Pax 2, PCR products were electrophoresed on 1.8% agarose gels and transferred to nylon membranes according to the manufacturer's instructions (Qiabrane Nylon Plus, Qiagen). Filters were hybridised with a 1.3 kb human Pax 2 cDNA probe (101398, kindly donated by The Max Planck Institut, Goettingen) labeled with [$^{32}$P]dCTP using a Rediprime® random primer labelling kit (Amersham) and ExpressHybe® (Clontech) according to the manufacturers' instructions. The filters were then exposed to x-ray film overnight.

Results

Figure 1B:
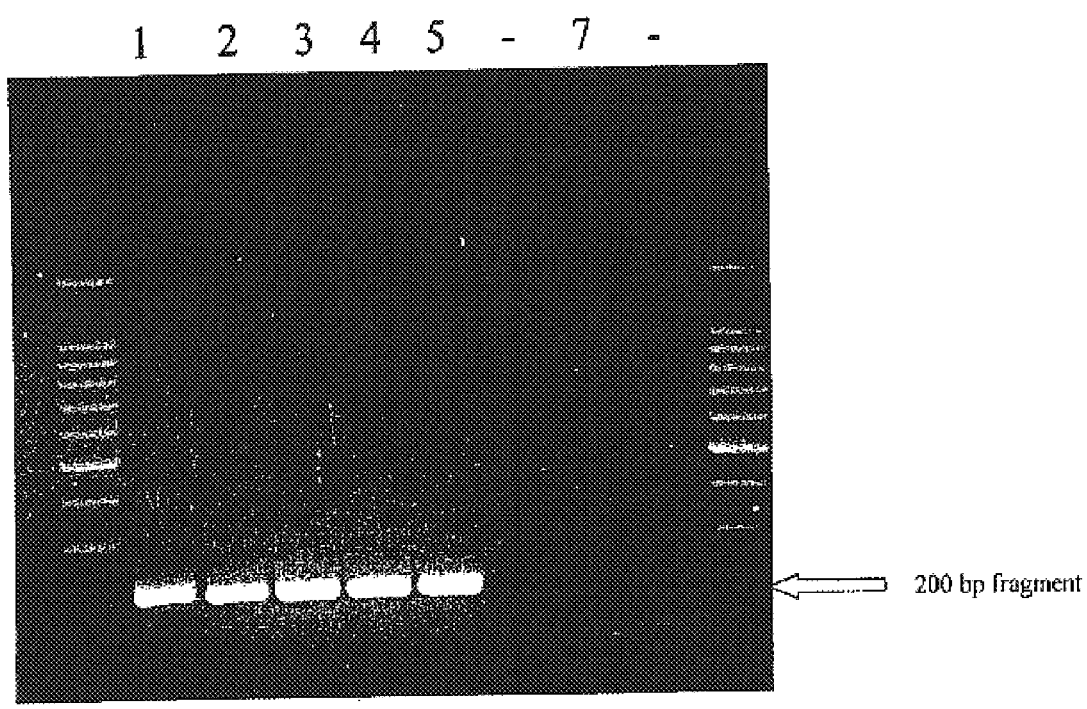
Figure 2A:
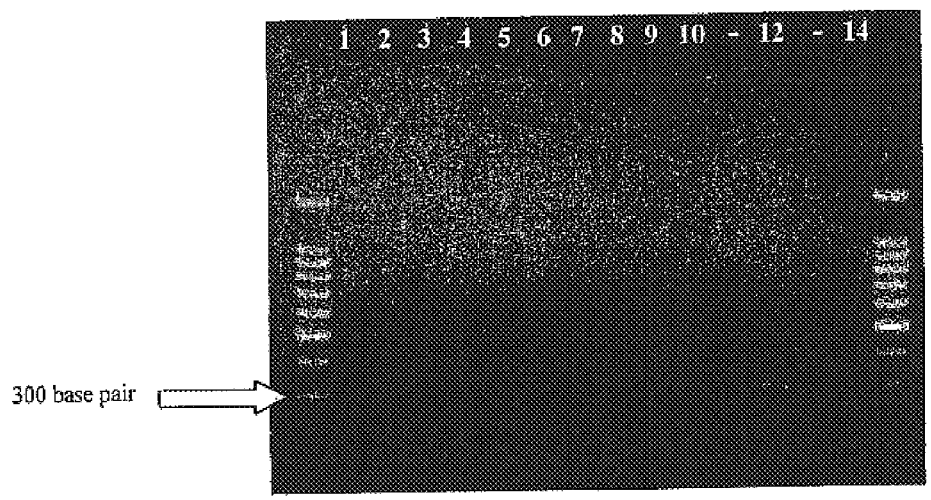
Figure 2B:
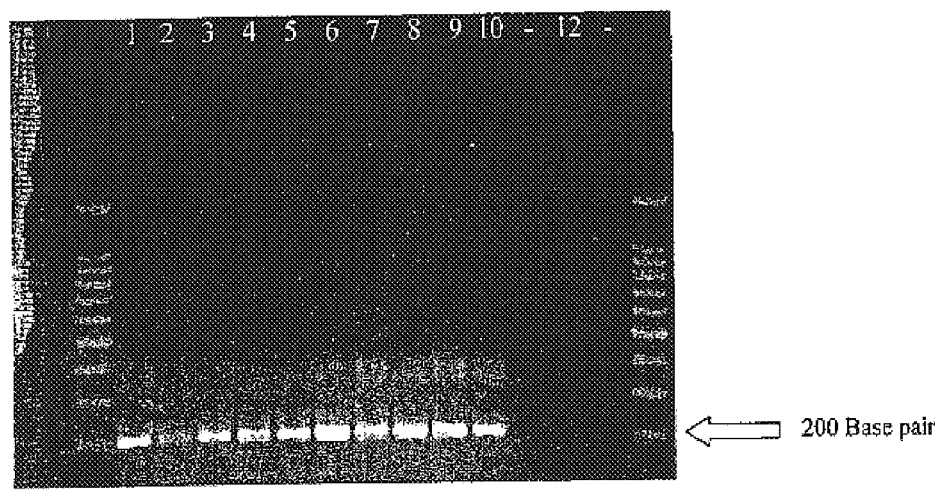

Cell lines. All 3 of the established prostate cancer cell lines LNCaP, DU-145 and PC-3 expressed Pax 2 transcript, reproducible on two separate RNA extractions (FIG. 1).

Pax 2 expression in prostate cancer samples. Pax 2 cDNA was amplified using PCR and expression was found in 3 of the 5 channel TURP tumour samples examined (60%). The stage of the tumours were the same and the grades (Gleason score) were similar, as shown in Table 1.

Pax 2 expression was clearly detected in 10 out of the 15 radical prostatectomy samples as assessed by visualisation using ethidium bromide staining. Pax 2 expression was less clearly detected in a further two of the radical prostatectomy samples as assessed by visualisation using ethidium bromide staining.

In the five benign prostatic hyperplasia samples studied, Pax 2 transcript was not detectable.

These results indicate that Pax 2 expression is linked with prostatic cancer but not with benign prostatic hyperplasia. It is not considered likely that the Pax 2 expression is a response to the procedure used for obtaining the sample as the cancerous and non-cancerous samples were subjected to the same treatment and there was not evidence of any injury to the tissues preoperatively.

TABLE 1 gleason scores for channel TURF samples

| Sample | Gleason score |
| --- | --- |
| 1 (lane 2 in FIG. 1a) | 3 + 3 |
| 2 (lane 3 in FIG. 1a) | 3 + 2 |
| 3 (lane 4 in FIG. 1a) | 3 + 4 |
| 4 (lane 5 in FIG. 1a) | 4 + 4 |
| 5 (lane 6 in FIG. 1a) | 5 + 5 |

EXAMPLE 2

Clinical Screen

A sample may be collected in one or more of the following ways:

(1) sextent biopsy (needle biopsy taken at six different positions) collected as part of diagnostic work for suspected prostate carcinoma, (2) TURP "chips" of tissue taken when the prostate is reduced in bulk via the urethra (treatment for Benign Neoplastic Hyperplasia [BPH])

(3) whole gland plus lymph nodes taken from radical prostatectomy patients (only useful for decisions regarding adjuvant treatment)

It is preferred that one of the above procedures for obtaining a sample is used. However, a non or less invasive test material (for example cells from urine, blood or semen) may be also be used.

Useful procedures may be described in Grizzle, "Tissue resources in the detection and evaluation of Markers" from Srivasiava et al "Early Detection of Cancer: Molecular Markers" Armenk Futura Publishing Co, Inc (1994); Jepsen & Bruskewitz(1998) "Recent developments in the surgical management of benign prostatic hyperplasia" Urology 51 (suppl 4A), 23–31; Bostwick & Dundore "Biopsy pathology of the prostate" (1997), published by Chapman & Hall Medical, London, particularly pages 19 to 25, all incorporated herein by reference.

EXAMPLE 3

Protein Analysis Using Western Blotting

The protein expression of PAX2 in the prostate cancer cell lines and tissue specimens was also analysed using western blotting. Briefly, the protein was extracted using TRIZOL® Reagent, the samples were size separated on a polyacrylamide gel and electrophoretically transferred to nitrocellulose membranes, and finally, the protein was detected using chemilumescence.

Protein Extraction

Protein was extracted from the interphase and organic phase saved from RNA extraction according to the manufacturer's instructions. Per 1 ml of TRIZOL® Reagent used for initial homogenisation, 0.3 ml of 100% ethanol was added. The samples were stored at room temperature for 3 minutes and then centriged at 2,000×g for 5 minutes at 2 to 8° C. The resultant DNA pellet was saved at −20° C. The phenol-ethanol supernate that contains the protein was transferred into a new tube. Following this, the protein was precipitated out of solution by adding 1.5 ml isopropanol per 1 ml of TRIZOL® Reagent originally used. The samples were then stored at room temperature for 10 minutes at 2 to 8° C. The protein pellet thus obtained was washed three times in a solution of 0.3 M guanidine hydrochloride in 95% ethanol. During each wash cycle, the protein pellet was stored in the wash solution for 20 minutes at room temperature and centrifuged at 7,500×g for 5 minutes at 2 to 8° C. After the third wash, the pellet was vortexed and stored at room temperature in 2 ml of ethanol for 20 minutes, and then centrifuged at 75,000×g for 5 minutes at 2 to 8° C.

The protein pellet was vacuum dried for 10 minutes and then dissolved in 1×SDS. The samples were then stored at −20° C.

Polyacrylamide Gel Electrophoresis

The proteins were size separated using the NOVEX™ NUPAGE Bis-Tris Electrophoresis System (San Diego, USA) 4–12% Bis-Tris Gels were used since, according to the manufacturer, this concentration provided the best separation for identification of a 48 KDa protein (MW of PAX2).

The samples were prepared by adding 0.7 $\mu$l of 0.1M DTT and 5 $\mu$l of NuPAGE LDS sample buffer to 14.3 $\mu$l of the protein solution. The resultant 20 $\mu$l of the samples was incubated with 4 $\mu$l of the marker at 99° C. for 4 minutes, chilled on ice and were electrophoresed on a gel. Two preparations of each sample were prepared and electrophoresed on two gels at the same time in the electrophoresis tank for 60 minutes at 200 V. Following this, one of the gels was silver stained to check for the presence of protein and its separation. The second gel was blotted onto a nitrocellulose membrane. The protein marker used was Rainbow molecular weight marker (Amersham Pharmacia Biotech, UK).

Silver Staining

The protocol is based on the method developed by Bloom and colleagues (Bloom et al. 1987, *Electrophoresis* 8, 93–99). The protein in the gel was fixed in 50 ml of formaldehyde fixing solution by continuous agitation on the shaker for 10 minutes. The gel was then washed twice with water, 5 minutes for each wash. Following this, the gel was soaked in 50 ml of 0.2 g/liter sodium thiosulphate and then washed twice with water, 20 seconds for each wash. It was then soaked for 10 minutes in 50 ml of 0.1% silver nitrate and washed with water. Following this, the gel was soaked in 50 ml of freshly made thiosulphate developing solution for 5 minutes until the bands were seen to intensify, then 2.5 ml of 2.3M citric acid was added to the solution. After 10 minutes the gel was washed in water by slow agitation for 10 minutes and then soaked in 50 ml of drying solution for 10 minutes.

The gel was then placed on a piece of Whatman paper and covered with cling film. It was then dried under vacuum at 60° C. for 2 hours.

Western Blotting

The proteins, size separated on the polyacrylamide gel, were electrophoretically transferred onto a nitrocellulose membrane using a modified version of the method described by Towbin et al (Towbin et al 1979 *P.N.A.S. USA*, 76, 4350–4354).

The transfer buffer was pre-prepared and chilled at 4° C. Following electrophoresis, the gels were rinsed in transfer buffer prior to blotting to facilitate the removal of electrophoresis salts and detergents. A piece of nitrocellulose membrane and two pieces of Whatman paper were cut to the dimensions of the gel. The membrane was soaked in the transfer buffer for 15 minutes. The Whatman paper and filter pads (provided with the tank) were also soaked in the transfer buffer.

The blot was set up by placing the gel on the nitrocellulose membrane with a Whatman paper on each side; a filter pad was then placed on either side of this. It was ensured that no air bubbles were trapped between the layers. These layers were then placed between two plastic panels (provided with the transfer tank) and clamped together.

The cassette was then placed in the transfer tank such that the nitrocellulose membrane was closer to the anode. The tank was filled with transfer buffer and was connected to the power supply. The transfer was performed at 60 V for three hours at 4° C.

Once the electrophoretic transfer was complete, the nitrocellulose membrane was removed and marked appropriately to identify its correct orientation. The blots were either used immediately or air-dried and stored in a refrigerator for future use.

Protein Detection by Chemiluminescence

Immunodetection was performed using the ECL™ Western blotting detection kit (Amersham Pharmacia Biotech, UK). The kit contains Solution 1 and Solution 2, which are added to each other in equal volumes just prior to use. The solutions contain a preacid (carboxylic acid with an extra oxygen), luminol and enhancer. The peroxidase conjugated to the streptavidin (see below) oxidises the preacid. In the presence of luminol and enhancer, the oxidised form of the enzyme emits light which can be detected by X-ray film.

For detection of the PAX2 protein, the primary antibody used was polyclonal rabbit anti-PAX2, the secondary antibody was biotinylated goat anti-rabbit IgG and streptavidin-peroxidase (horseradish peroxidase) conjugate. All the antibodies are diluted in Tris-buffered saline with 0.1% Tween 20 and 1% low fat dried milk. The other solutions used for immunodetection were, Tris-buffered saline (TBS) TBS with 0.1% Tween 10 (TBS-T) and blocking solution (5% low fat dried milk in TBS-T).

The chemiluminescence immunodetection was carried out according to the manufacturer's instructions, which are summarised here. The procedure was carried out at room temperature, and the incubations and washes were performed on an orbital shaker. In order to determine the optimum concentration of antibodies needed, a series of experiments were performed with varying concentrations of antibodies. The concentration of antibodies that produced the clearest bands for PAX2 with the least number of non-specific bands were chosen. Gel electrophoresis was performed using the positive control (UOK-117) only, the gel was then Western blotted. The Western blot was cut into strips, each representing one lane of the original gel.

Following the protocol below, the membrane was incubated with different concentrations of antibodies and the optimum concentration for each antibody was chosen. The dilution of primary antibody used ranged from 0.2 to 1.6 $\mu$g.ml (optimum was 1.0 $\mu$g/ml). The dilutions of secondary antibody used, ranged from 1 in 5,000 to 1 in 20,000 (the optimum dilution was 1:12,000). The range of HRP-streptavidin dilutions used were from 1 in 5,000 to 1 in 20,000 (the best results were obtained with 1:18000 dilution).

The Western blots were soaked in the blocking solution for 1 hour. Following this, they were rinsed twice in TSB-T, then washed in TSB-T for 15 minutes and then twice for 5 minutes. The blots were then incubated in 1 µg/ml of primary antibody for 1 hour and washed in TBS-T as detailed above.

Following the wash, the blots were incubated in 1 in 12,000 dilution of secondary antibody for one hour and the washing step was repeated. The blots were incubated with a 1 in 18,000 dilution of HRP-Streptavidin conjugate for 45 minutes and then washed 1×15 minutes and 4×5 minutes in fresh changes of TBS-T. The blots were removed from the wash solution and excess buffer was drained off. They were placed on a piece of cling-film with the protein side up. The detection reagent (mixed as detailed above) was added to the protein side of the membranes. The blots were incubated with the detection reagent for 1 minute. The excess detection reagent was drained off and the membranes were wrapped in cling film. The membranes, protein side up, were placed in a film cassette and exposed to X-ray films. The exposure time varied from 10 to 30 seconds depending on the strength of signal.

What is claimed is:

1. A method of diagnosing prostate cancer in a human patient comprising the steps of:
   (i) obtaining a sample containing mRNA from a test sample of prostate cells from the patient;
   (ii) detecting the presence or absence of Pax 2 mRNA expression which is associated with prostate cancer; and
   (iii) diagnosing the presence of prostate cancer in the event that the presence of Pax 2 mRNA expression which is associated with prostate cancer is detected in the test sample.

2. A method of identifying the presence of metastatic prostate cancer in a human patient comprising the steps of:
   (i) obtaining a sample containing mRNA from a test sample of prostate cells from the patient; and
   (ii) detecting the presence or absence of Pax 2 mRNA expression which is associated with metastatic prostate cancer; and
   (iii) diagnosing the presence of metastatic prostate cancer in the event that the presence of Pax 2 mRNA expression which is associated with metastatic prostate cancer is detected in the test sample.

3. A method according to any of claims 1 or 2 wherein the cancer is invasive.

4. A method according to any of claims 1, or 2 wherein the sample contains mRNA and the amount of Pax 2 mRNA is measured by contacting the mRNA with a nucleic acid which hybridises selectively to Pax 2 mRNA.

5. A method according to claim 4 wherein the nucleic acid which hybridises is detectably labelled.

6. A method according to claim 4 wherein the nucleic acid which selectively hybridises is detectably labelled.

7. A method according to claim 4 wherein the nucleic acid which selectively hybridises is suitable for use in a nucleic acid amplification reaction.

8. A method according to any of claims 1 or 2 wherein the sample is a sample of the tissue in which prostate cancer is suspected or in which prostate cancer may be or has been found, or is a sample of urine, semen, blood or lymph fluid containing cells from said tissue.

9. A method according to claim 1 wherein no Pax 2 mRNA is detectable in the sample of non-cancerous cells.

10. A method according to claim 2 wherein no Pax 2 mRNA is detectable in the sample of non-cancerous cells.

11. A method according to any one of claims 1, 2, 9 or 10, wherein the cancer is invasive.

12. A method according to any one of claims 1, 2, 9 or 10, wherein the sample contains mRNA and the amount of Pax 2 mRNA is measured by contacting the mRNA with a nucleic acid which hybridizes selectively to Pax 2 mRNA.

13. A method according to claim 12 wherein the nucleic acid which hybridizes is detectably labeled.

14. A method according to claim 12 wherein the nucleic acid which selectively hybridizes is detectably labeled.

15. A method according to claim 12 wherein the nucleic acid which selectively hybridizes is suitable for use in a nucleic acid amplification reaction.

16. A method according to any one of claims 1, 2, 9 or 10, wherein the sample is a sample of the tissue in which prostate cancer is suspected or in which prostate cancer may be or has been found, or is a sample of urine, semen, blood or lymph fluid containing cells from said tissue.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: PCR primer

<400> SEQUENCE: 1
tttgtgaacg gccggcccct a                                              21

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
cattgtcaca gatgccctcg g                                              21

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
ggccgtattg ggcgcctggt c                                              21

<210> SEQ ID NO 4
<211> LENGTH: 22
<212> TYPE: DNA
<213> ORGANISM: Artificial Sequence
<220> FEATURE:
<223> OTHER INFORMATION: PCR primer

<400> SEQUENCE: 4
gaagggcaac tactgttcga ag                                             22

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ggccgtattg gcgcctggtc                                                20